(12) United States Patent
Holladay

(10) Patent No.: US 7,964,833 B2
(45) Date of Patent: Jun. 21, 2011

(54) MULTI-FOCAL INTRAOCULAR LENS SYSTEM AND METHODS

(75) Inventor: Jack T. Holladay, Bellaire, TX (US)

(73) Assignee: Elenza, Inc., Roanoke, VA (US)

( * ) Notice: Subject to any disclaimer, the term of this patent is extended or adjusted under 35 U.S.C. 154(b) by 67 days.

(21) Appl. No.: 12/184,763

(22) Filed: Aug. 1, 2008

(65) Prior Publication Data

US 2009/0032679 A1 Feb. 5, 2009

Related U.S. Application Data

(60) Provisional application No. 60/953,640, filed on Aug. 2, 2007.

(51) Int. Cl.
G02B 7/04 (2006.01)
G02B 27/40 (2006.01)
G02B 27/64 (2006.01)

(52) U.S. Cl. .................. 250/201.2; 250/559.38; 356/3; 356/4.01

(58) Field of Classification Search .......... 250/201.1, 250/201.2, 559.38; 345/127, 128, 129, 130, 345/131, 147, 156, 201, 472.1, 472.2, 670, 345/671; 356/3, 4.01
See application file for complete search history.

(56) References Cited

U.S. PATENT DOCUMENTS

| 5,276,539 | A | 1/1994 | Humphrey |
| 6,638,304 | B2 | 10/2003 | Azar |
| 7,061,693 | B2 | 6/2006 | Zalevsky |
| 2005/0030322 | A1* | 2/2005 | Gardos .................. 345/667 |
| 2006/0095128 | A1 | 5/2006 | Blum et al. |
| 2007/0106376 | A1 | 5/2007 | Roberts et al. |
| 2007/0168027 | A1 | 7/2007 | Brady et al. |

OTHER PUBLICATIONS

The Search Report and Written Opinion corresponding to the PCT/US08/71957 application dated Nov. 4, 2008.

* cited by examiner

*Primary Examiner* — Thanh X Luu
*Assistant Examiner* — Francis M Legasse, Jr.
(74) *Attorney, Agent, or Firm* — Kilpatrick Townsend & Stockton LLP

(57) ABSTRACT

The invention pertains to methods, components, and operations of multi-focal intraocular lens systems, including range finding for driving same and for discriminating between multiple objects and varying brightness conditions. The invention also pertains to intraocular photosensors and range-finding methods to be used with intra-ocular lens systems, and components, that provide multi-focal IOL capabilities in dynamic visual environments.

18 Claims, 19 Drawing Sheets

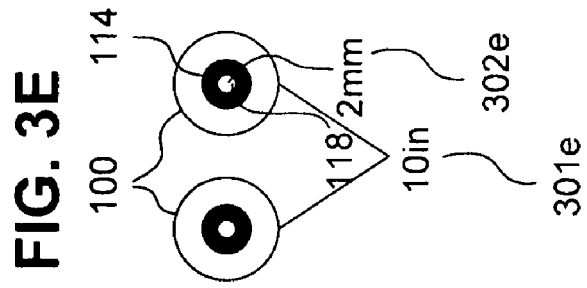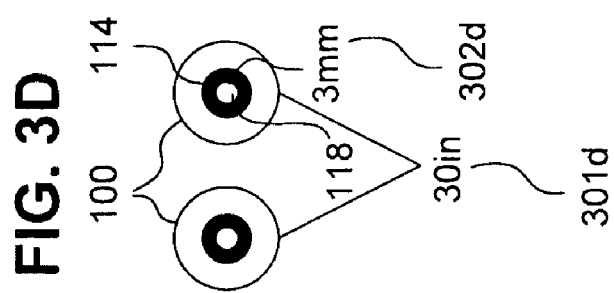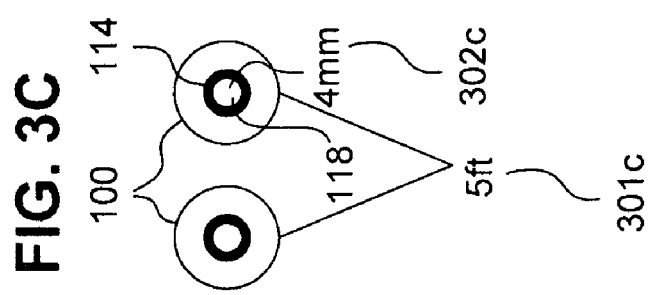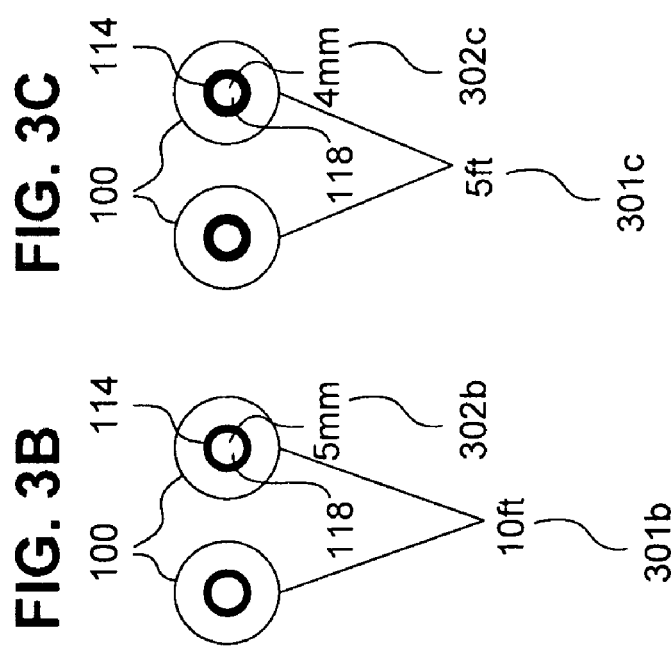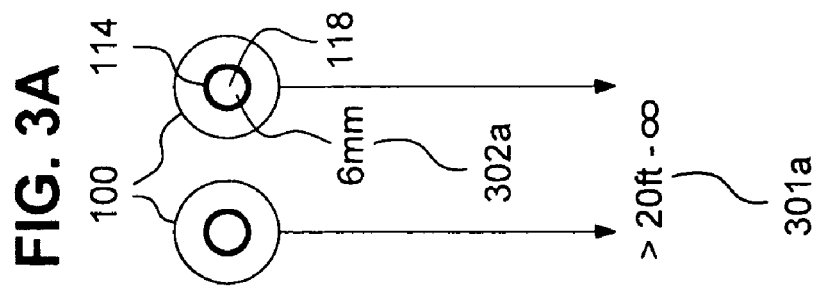

Population Group: 20 Year Olds
Object Distance in meters (convergence power in Diopters)

| Relative Brightness | 6 m (0 D) | 2 m (0.5 D) | 1 m (1 D) | 0.5m (2 D) | 0.25m (4 D) |
|---|---|---|---|---|---|
| 1 ft-C (~10 lux) | 7 mm | 5.6 mm | 4.3 mm | 3 mm | 2 mm |
| 100 ft-C (~1000 lux) | 4.5 mm | 3.9 mm | 3.2 mm | 2.6 mm | 2 mm |
| 2500 ft-C (~25000 lux) | 3 mm | 2.8 mm | 2.5 mm | 2.2 mm | 2 mm |

FIG. 4A

Population Group: 70 Year Olds
Object Distance in meters (convergence power in Diopters)

| Relative Brightness | 6 m (0 D) | 2 m (0.5 D) | 1 m (1 D) | 0.5m (2 D) | 0.25m (4 D) |
|---|---|---|---|---|---|
| 1 ft-C (~10 lux) | 5 mm | 4.5 mm | 4 mm | 3.1 mm | 2.5 mm |
| 100 ft-C (~1000 lux) | 4 mm | 3.6 mm | 3.1 mm | 2.8 mm | 2.5 mm |
| 2500 ft-C (~25000 lux) | 3 mm | 2.9 mm | 2.8 mm | 2.6 mm | 2.5 mm |

FIG. 4B

Population Group: 40 Year Olds
Object Distance (convergence power)

| Relative Brightness | 6 m (0 D) | 2 m (0.5 D) | 1 m (1 D) | 0.5m (2 D) | 0.25m (4 D) |
|---|---|---|---|---|---|
| 1 ft-C (~10 lux) | 6 mm | 5.1 mm | 4.2 mm | 3.3 mm | 2.3 mm |
| 100 ft-C (~1000 lux) | 4 mm | 3.5 mm | 3.1 mm | 2.7 mm | 2.3 mm |
| 2500 ft-C (~25000 lux) | 3 mm | 2.8 mm | 2.6 mm | 2.4 mm | 2.3 mm |

FIG. 4C

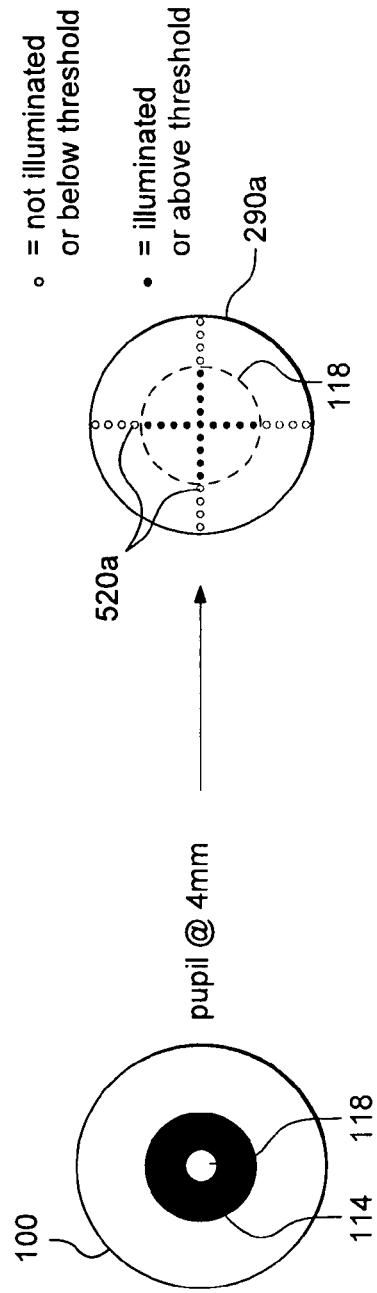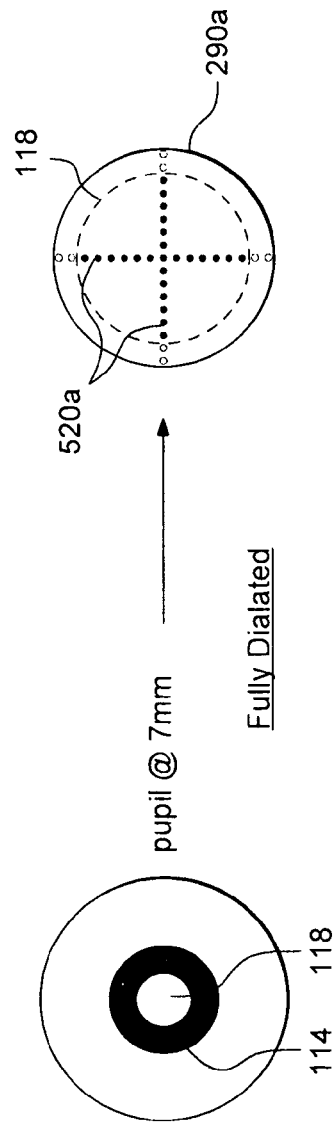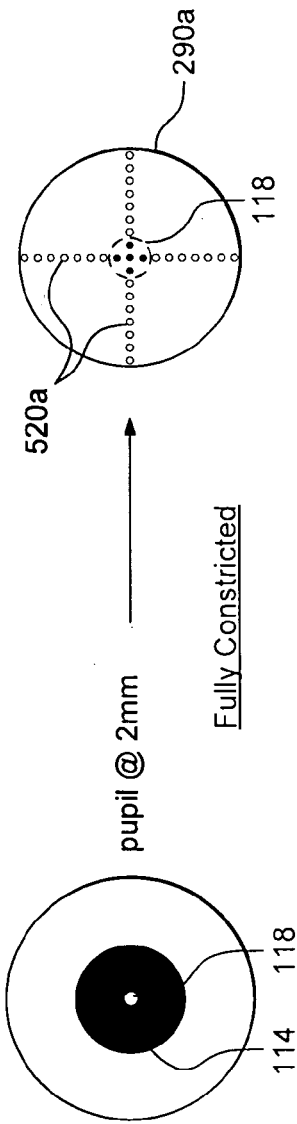
FIG. 6A  pupil @ 4mm
FIG. 6B  pupil @ 7mm  Fully Dialated
FIG. 6C  pupil @ 2mm  Fully Constricted
○ = not illuminated or below threshold
● = illuminated or above threshold

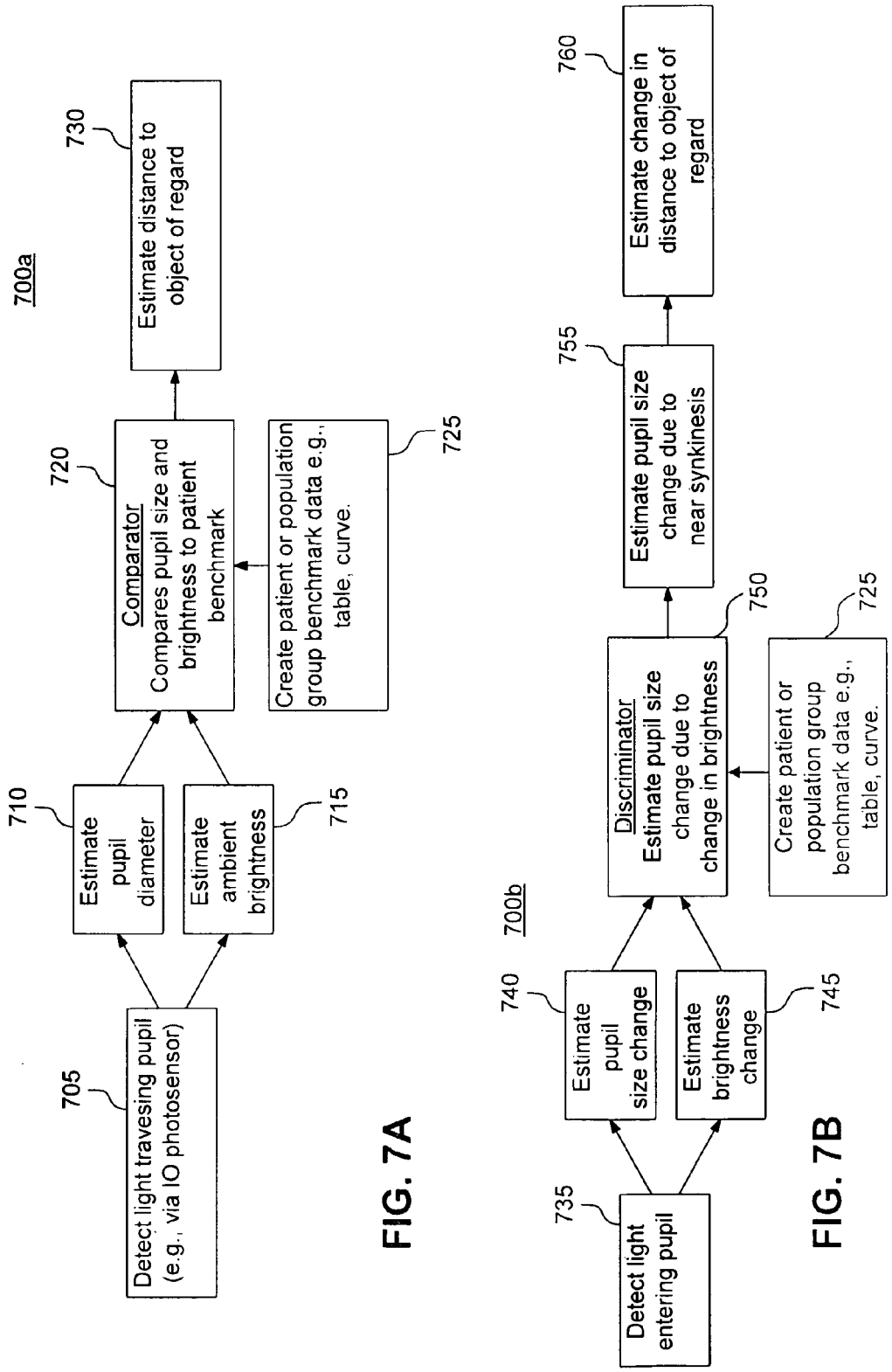

Pupil Size and Relative Brightness as measured by IO photosensor
(object distance table)

| Relative Brightness | Pupil Size | | | | | | | | | |
|---|---|---|---|---|---|---|---|---|---|---|
| | 5mm | 4.7mm | 4.4mm | 4.1mm | 3.8mm | 3.5mm | 3.2mm | 2.9mm | 2.7mm | 2.5mm |
| 0.01 ft-C (~0.10 lux) | 6m | 5m | 4m | 3m | 2m | 1m | 0.8m | 0.6m | 0.4m | 0.25m |
| 1 ft-C (~10 lux) | 6m | 4m | 2m | 1.2m | 0.9m | 0.7m | 0.5m | 0.4m | 0.3m | 0.25m |
| 20 ft-C (~200 lux) | X | 6m | 4m | 2m | 1m | 0.8m | 0.6m | 0.4m | 0.3m | 0.25m |
| 100 ft-C (~1000 lux) | X | X | X | 6m | 3m | 2m | 1m | 0.7m | 0.5m | 0.25m |
| 500 ft-C (~5000 lux) | X | X | X | X | X | 6m | 2m | 1m | 0.5m | 0.25m |
| 2500 ft-C (~25000 lux) | X | X | X | X | X | X | 6m | 2.5m | 0.8m | 0.25m |
| 5000 ft-C (~50000 lux) | X | X | X | X | X | X | X | 6m | 2m | 0.25m |

FIG. 7C

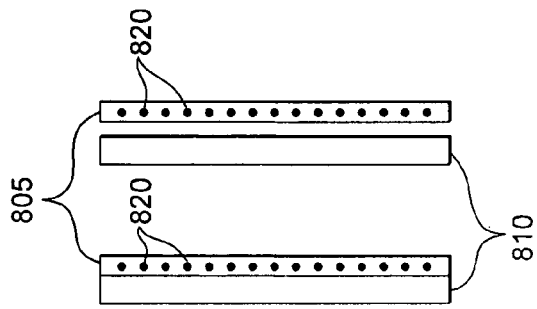
FIG. 8B
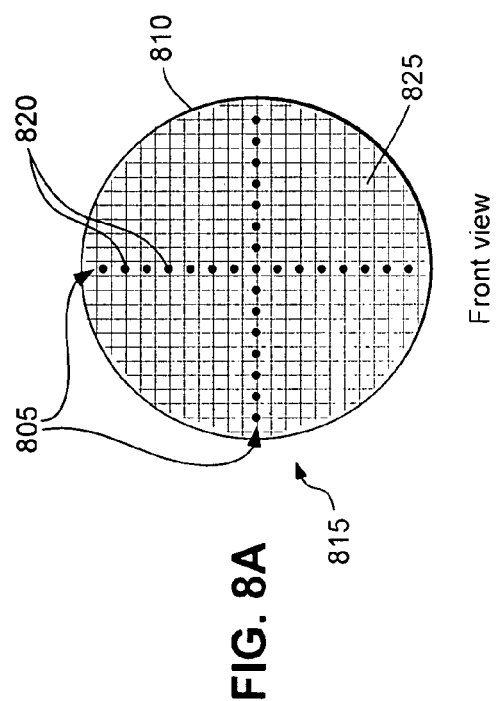
FIG. 8A
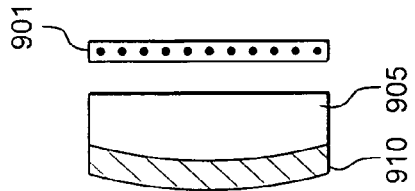
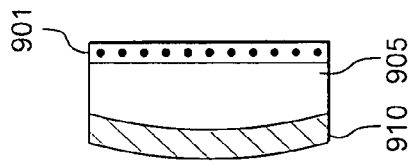
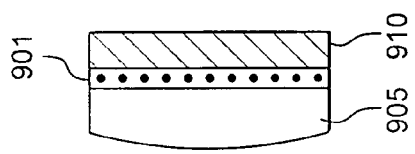
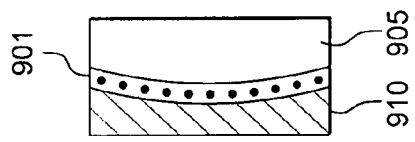
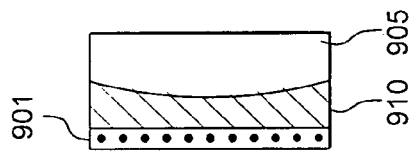
FIG. 9

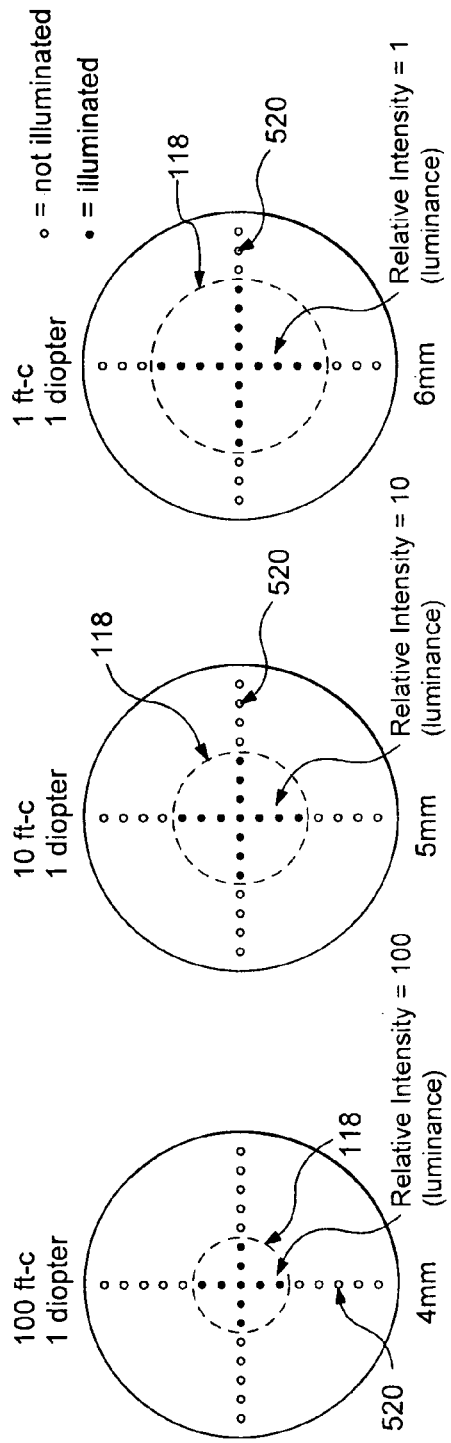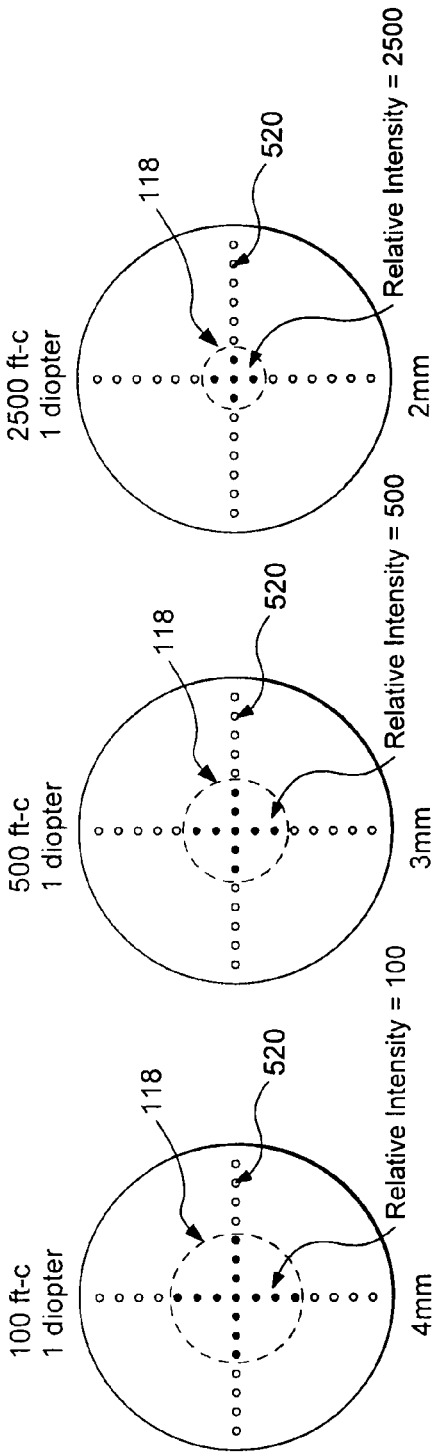

MULTI-FOCAL INTRAOCULAR LENS SYSTEM AND METHODS

CROSS REFERENCE TO RELATED APPLICATION

This application claims priority to and benefit of, U.S. Provisional Patent Application Ser. No. 60/953,640, filed Aug. 2, 2007, the contents of which are incorporated herein by reference.

FIELD OF INVENTION

Example aspects of the present invention generally relate to multi-focal intraocular lens ("IOL") systems, and more particularly to intraocular photosensors and range-finding methods to be used with IOL systems and components that provide multi-focal IOL capabilities in dynamic visual environments.

DESCRIPTION OF THE RELATED ART

In the human visual system, in order to selectively focus on nearby objects such as those less than 20 feet away, the focal length of an eye's lens must change. In a normal eye, this is achieved through the contraction of a ciliary muscle that is mechanically coupled to the lens. The extent of contraction of the ciliary muscle deforms the lens thereby changing the focal length, or power, of the lens. By selectively deforming the lens in this manner it becomes possible to focus on objects that are at different distances from the eye. This process of selectively focusing on objects at different distances is referred to as accommodation.

A diopter ("D") is a unit of measurement of the refractive power of lenses equal to the reciprocal of the focal length measured in meters. In humans, the total power of a relaxed eye is approximately 60 diopters. The cornea accounts for approximately two-thirds of this power and the crystalline lens contributes the remaining third. As humans age, the amplitude of accommodation reduces from approximately 15 to 20 diopters in the very young, to about 10 diopters at age 25, to around 1 diopter at 50 and over. In the case of a 50 year old and whose lens system can only provide 1 D of accommodative power, this means that the closest object on which the individual can clearly focus is at a distance of 1 meter (1 meter=1/1 diopter). Similarly, 2 D will allow accommodative focus on an object which is ½ meter distant, 3 D will allow focus on an object ⅓ meter distant, and so on.

The ability to accommodate or see clearly at near distances can be reduced or eliminated for a variety of reasons, including: injury, disease, or the natural aging process. For example, as a person ages, the natural crystalline lens of the eye loses plasticity and it becomes increasingly difficult to deform the stiffening lens to achieve accommodation sufficient to focus on objects at different nearby distances.

Cataract is a disease associated with aging in which the natural crystalline lens becomes cloudy and more opaque, reducing vision significantly. Cataracts typically occur after the loss of accommodation. Intraocular lenses ("IOLs") have been used in the United States since the late 1960s to restore vision to patients suffering this disease, and more recently are being used in several types of refractive eye surgeries. IOLs are typically permanent, plastic lenses that are surgically implanted inside of the eyeball to replace or supplement the eye's natural crystalline lens.

IOLs can also serve to compensate for loss of refractive function of the human eye. Accommodative IOLs have been introduced, for example, which change focus by movement (e.g., physically deforming and/or translating within the orbit of the eye) as the muscular ciliary body reacts to an accommodative stimulus from the brain, similar to the way the body's natural crystalline lens focuses. Unfortunately, these types of accommodative IOLs are substantially inferior in performance when compared to a healthy natural crystalline lens, and fail to have the capability to accurately and reliably focus on demand.

An IOL system that will be capable of accommodation and that can dynamically adjust its focal length on objects of varying distances should be able to accurately determine the distance to the object of focus, also commonly referred to as the object of regard. That is, to be able to adjust the focus of the visual system in order to bring near objects of regard in optimum focus, the distance to the object of regard should be known.

In order to achieve accurate multi-focal capabilities, e.g., accommodation, an IOL system should also be able to rapidly and accurately determine the distance to the object of regard on an intermittent and preferably continuous basis so that the dynamically focusing lens system can adjust to the proper focus based on the distance to the object of regard.

There have been several methods proposed for determining the distance to the object of regard, or range-finding. Examples include using a radar-like approach, where an infrared beam and sensor are incorporated into a lens system and used to detect or target distance through transmission, reflection, sensing, and signal processing. Another proposed range-finding technique uses a piezo-electric crystal attached to the ciliary muscle and infers the distance to the object of regard by the voltage generated by the crystal in response to degree of the ciliary muscle contraction that accompanies and purportedly indicates the degree of accommodation sought by the visual system. The ciliary body is known to be very fragile and difficult to work with, however, making these solutions relatively complex and unappealing.

Other proposed range-finding methods involve repeatedly measuring the contrast of an image while the focus of the optical system is continuously adjusted until a contrast maximum is detected at which point the object is considered in focus. A significant problem with this approach, however, is that often there are multiple objects in the line of vision, making it difficult or unable to distinguish between the desired object of regard and an intervening object (e.g., raindrops).

A need exists for an accurate and reliable way to determine the distance to an object of regard in an accommodative IOL system and to discriminate between various visual ambient conditions such as lighting variations and multiple objects. A further need exists for a range-finder that can be simply integrated into an IOL system and which does not negatively impact the visual system either anatomically, physiologically, or with respect to acuity. Yet another need exists for a dynamic multi-focal IOL system including a range-finding component capable of discriminating between distances to objects of regard in various ambient lighting conditions and for distinguishing changes in ambient lighting conditions.

SUMMARY OF THE INVENTION

In one embodiment, an intraocular photosensor design is used to measure pupil diameter, and changes thereto, by detecting changes of incident light intensity and distribution through the pupil to determine the pupil size. In this embodiment a photosensor is placed posterior and directly in line with the pupil, in a relatively coplanar relationship. One or more linear arrays of photosensitive elements are included, the number of elements being sufficient to discriminate between pupil size changes, while the photosensor remains sufficiently transparent.

In one embodiment, the pupil size determination is used to estimate a distance to an object of regard based on a relationship between the pupil size and ocular convergence, or near-synkinesis. In another embodiment, the determined distance to the object of regard is used as input to drive a dynamically focusable intraocular lens system in order to bring the object of regard in or near focus. In a further embodiment the programmable photosensor is utilized as the primary range-finder in an IOL system. In yet another embodiment, the determination of the pupil size is used as a supplemental or complementary method of range finding, or for determining the distance to objects of regard.

In another embodiment the sensor is integrated with an intraocular lens system. The intraocular lens system is a multi-focal lens system in one embodiment, and may comprise electroactive lens elements, or other multi-focal lens configurations, and further comprises a microcontroller, actuator, and power supply means for controlling, actuating, and powering the lens system. In an embodiment, the photosensor is integrated with an electroactive pixelated array lens system capable of sensing incident light in order to determine pupil size, determine object distance, and adjust the focal power of the lens system to focus on the object. In another embodiment, the photosensor is integrated with a non-pixelated electroactive lens system. In still another embodiment, the photosensor is integrated with or a component of a non-electroactive focusing system.

One embodiment of the invention comprises an intraocular lens system comprising, a multi-focal lens system for adjusting the power of the focal system, a range-finder for determining the distance to the object of regard, a controller and actuator for controlling and driving the multi-focal lens system, and a power source for powering the components of the system. In one embodiment, the range-finder comprises an intraocular photosensor and associated processing means for determining the distance to an object of regard based on pupil diameter. In another embodiment, the range finder comprises a photosensor which utilizes range-finding technologies such as contrast measurements techniques, in addition to pupil size measurement to more accurately and reliably determine the distance to the object of regard. In another embodiment, the photosensor is integral with the lens system. In still another embodiment, the photosensor is a physically separate and modular component of the overall system. In one embodiment, the photosensor is placed posterior to the IO lens. In another embodiment, the photosensor is place anterior to the intraocular ("IO") lens.

In one embodiment, the innovative photosensor measures and determines both the light intensity and distribution traversing the pupil, and the change in light intensity received at individual sensor elements. By measuring the light distribution, and change in light distribution, on the photosensor array, the size of pupil is determined. By measuring the temporal change in light intensity of illuminated sensor elements, any changes in the ambient brightness is also determined. In this embodiment, the changes in pupil size due to both the brightness reflex and the near synkinesis reflex can be determined, and the photosensor and range-finding apparatus can distinguish between both changing light conditions and changes to the distance to the object of regard. As discussed below, the ability to detect changes in relative light levels can be used to distinguish between pupil reflex responses due to both brightness and synkinesis causes and can thereby accurately determine changes in ambient brightness levels as well as the distance to an object of regard.

In one embodiment, the pupil sizes of individual patients are measured for a variety of brightness and ocular convergence scenarios and a baseline established relating pupil size to various lighting and convergence combinations. This baseline is used to program an implantable and custom IO photosensor, or integrated IO lens system such that accurate object distances can be determined and accurate focus achieved for each patient to take into account the idiosyncratic pupilary response. In another embodiment, only the synkinetic converge response is measured and used to establish a baseline relating pupil size to object distance. In still another embodiment, standardized pupilary response baselines are created for sub-population groups, and these baselines are used to program a standardized IO range-finder and system.

These and other features and objects of the invention will be more fully understood from the following detailed description of the preferred embodiments that should be read in light of the accompanying drawings.

BRIEF DESCRIPTION OF THE DRAWINGS

The accompanying drawings, which are incorporated in and form a part of the specification, illustrate the embodiments of the present invention and, together with the description serve to explain the principles of the invention. In the drawings:

FIGS. 3A-F show examples of ocular convergence and the pupilary synkinetic convergence reflex for various degrees of convergence, and examples of the brightness reflex response of the pupil to varying brightness conditions;

FIGS. 4A-C depict tabulated data showing the estimated pupil sizes at various brightness levels and convergence conditions for different population groups according to one embodiment of the present invention;

FIGS. 6A-E show a front view of the photosensor of FIG. 5A and its elements, implanted behind a pupil, in various states depending on the size of the pupil according to example embodiments of the present invention;

FIG. 7A shows a process for determining the distance to an object of regard according to one embodiment of the present invention;

FIG. 7B shows an example process for determining the distance to an object of regard according to one embodiment of the present invention;

FIG. 7C shows an example look-up table for determining distance to an object of regard according to one embodiment of the present invention;

FIGS. 8A-B show examples of a sensor array and electroactive lens integrated onto a single chip according to various embodiments of the present invention;

FIG. 9 shows example positions of a photosensor integrated with or adjacent to a single electroactive lens according to various embodiments of the present invention;

FIGS. 14A-F show the photosensor and its elements in various states depending on the size of the pupil and the ambient light intensity according to one embodiment of the present invention.

DETAILED DESCRIPTION

Figure 1:
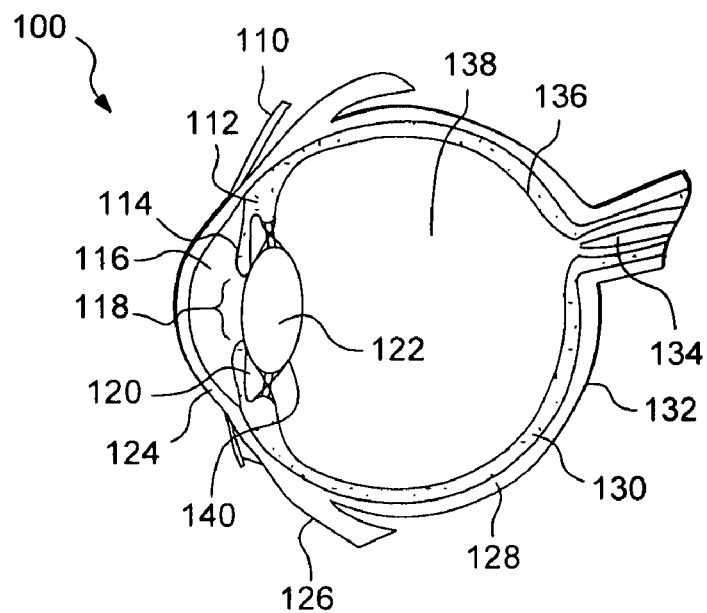
FIG. 1 shows the anatomical structure of the eye.

FIG. 1 shows the anatomical structure of the eye 100 with labels, including: conjunctiva 110; ciliary body 112; iris 114; pupil 118; anterior chamber 116 (containing aqueous humour); crystalline lens 122; cornea 124; extraocular muscle 126; scelera 128; choroid 130; macula 132; optic nerve 134; retina 136; vitreous humor 138; and capsular bag 140. The crystalline lens 122 is encapsulated by a capsular bag 140. During a typical lens replacement surgery, the natural lens 122 is removed from the capsular bag 140, and the new IOL is implanted inside the capsular bag 140 by well known surgical techniques. The IOL can be inserted in a folded condition and then unfolded once inside the capsular bag 140.

Figure 2A:
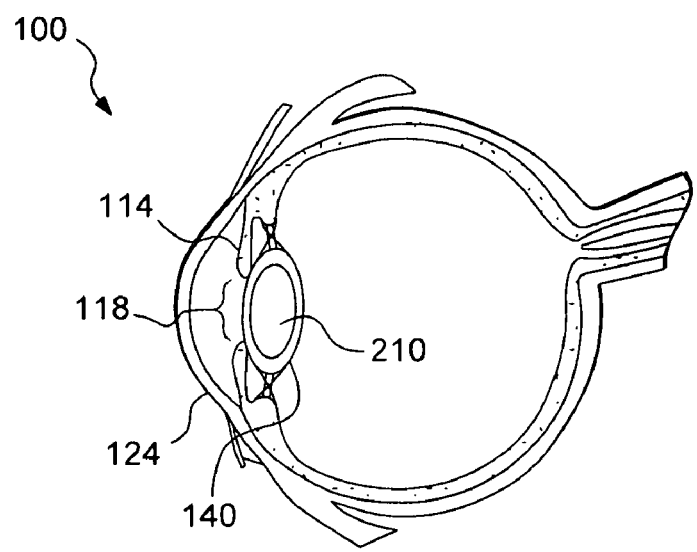
FIGS. 2A-B show an example IOL system and implant according to one embodiment of the present invention.
Figure 2B:
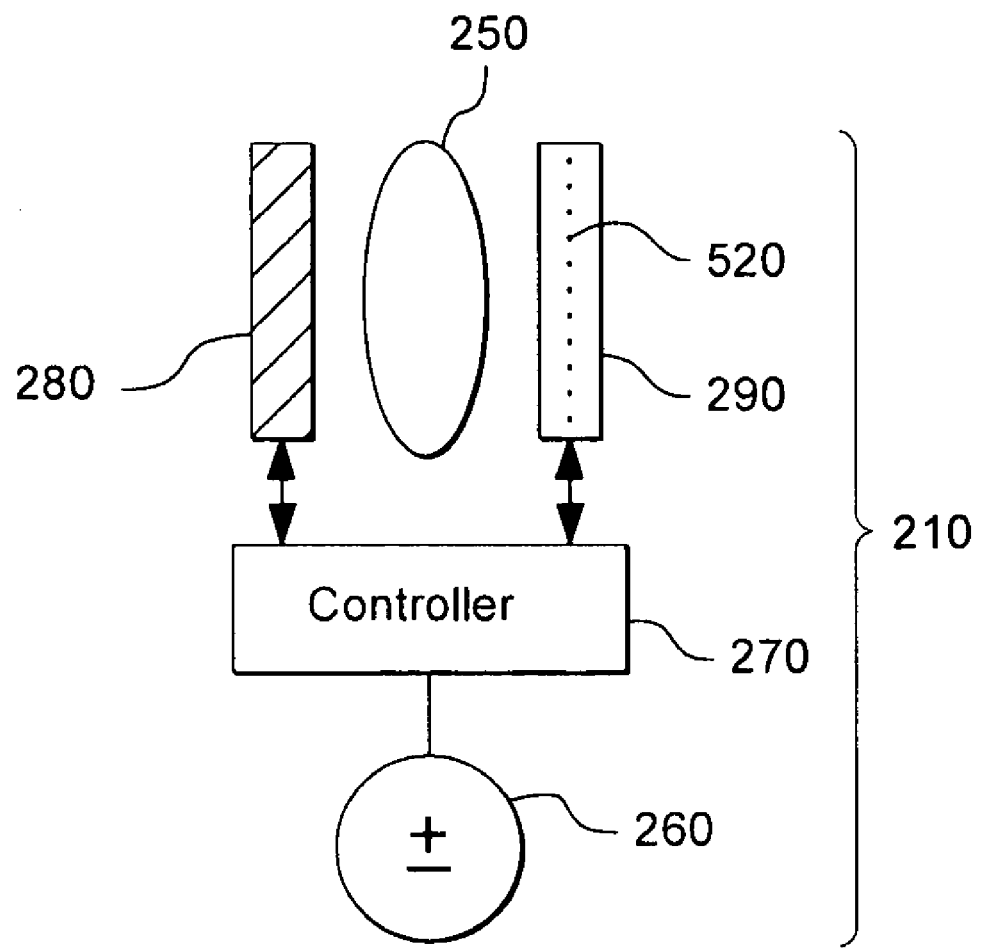

FIG. 2A shows an example of a multi-focal IOL system 210 implanted inside the capsular bag 140. FIG. 2B illustrates a blow up of the IOL system 210 shown in FIG. 2A. Referring to FIG. 2B, in one embodiment, the implanted IOL system 210 includes an electroactive lens 250 having electroactive elements capable of changing its refractive index in response to an applied voltage 260. A controller 270 determines the necessary control signals to be sent to the electroactive lens 250, and an actuator 280 drives the electroactive lens element 250 via electrodes to alter its refractive index. In this embodiment, a photosensor chip 290 having photosensitive elements 520 (also referred to as photosensitive elements) is configured in the form of a programmable range-finder which is integrated with the lens system 210. The photosensor chip 290 (also referred to as a range-finder photosensor or simply range-finder), described in more detail below, operates by detecting the areal distribution of incident light that has traversed through the pupil 118 and estimating the size of the pupil 118 based on the incident light distribution.

The pupil 118 is essentially circular and the amount and distribution of light passing through the pupil 118, having undergone significant refraction by the cornea 124, can be effectively represented as a circular beam having a radius equal to that of the pupil 118. As discussed in more detail below, the pupil size is used to estimate the distance to an object of regard, and based on this estimation, the controller 270 determines the appropriate focal length needed to bring the object in focus and causes the actuator 280 to actuate the electroactive lens 250, changing its effective refractive index in order to bring the object of regard in focus (on the retina 136). The relative changes of ambient brightness can also be measured by the range-finder photosensor 290 and used to distinguish between and account for pupil size changes resulting from different pupil reflex responses.

The above description is that of one embodiment only. Various other embodiments, including different types of electroactive and non-electroactive multi-focal lens systems are contemplated. For example, the IOL system components can also be modular and elements of the system can be placed outside the capsular bag 140 and even outside the eye 100. The details of the methods for determining the distance to the object of regard and a variety of photosensor and IOL system designs are now described.

FIGS. 3A-E illustrate various degrees of ocular convergence and corresponding pupil sizes 302a-e, which, as described below, are used to estimate object distance. The concept of ocular convergence is a measure of how the lines of sight of each of the eyes 100 cross when objects are viewed at near distances. Generally, distance vision means vision when viewing objects at a distance of greater than 20 ft (~6 meters) as shown in FIG. 3A (301a), and near vision means vision when viewing an object at less than 20 ft as shown in FIGS. 3B-3E (301b-301e). In a normal human visual system, the process and mechanism of bringing a near object (anything less than 20 ft) into focus is called accommodation, and during this process the eyes cross or converge onto the object. As shown in FIG. 3A (301a), there is zero convergence when viewing an object at a distance of greater than 20 ft (the line of sight of each of the eyes is effectively parallel to one another). As the object of regard is brought closer to the eyes, the degree of convergence increases as shown in FIGS. 3B-E (301b-301e).

Also shown in the illustrations is how the size (302a-302e) of the 118 pupil differs for different degrees of convergence. Changes in the pupil diameter can be effected by the opening and closing of the iris 114. This is a result of a well understood pupilary reflex response known as the synkinetic reflex response or "near synkinesis". Particularly, in this reflex, the pupil 118 changes its diameter in response to the crossing of the eyes, or ocular convergence. The greater the degree of convergence, the greater the contraction of the pupils. This is shown in FIGS. 3A-E (302a-302e), the change in pupil diameters corresponding to the degrees of convergence. More particularly, in FIG. 3A, when the object of regard is at a distance, of 20 ft or more, the eyes are generally parallel, exhibiting no degree of crossing or convergence, and the pupil synkinetic response is absent. As the object of regard is brought nearer, as shown in FIGS. 3B-3E, the degree of convergence increases and the pupil's contract causing their diameter to decrease. For instance, as shown in FIG. 3A, a pupil may be about 6 mm in diameter when viewing a distant object. When the viewer regards an object at a distance of 10 feet, as shown in FIG. 3B, the eyes converge and the pupils contract, for example to 5 mm. In FIG. 3C, when the viewer regards an object at 5 feet, the degree of convergence increases and the pupils contract to, for example to 4 mm. In FIGS. 3D and 3E, when the object viewed is for example 2.5 ft away, the eyes are even more crossed and pupils are even more constricted, e.g., 3 mm, and as the object is brought to 10 inches the pupils may contract to about 2 mm. The actual value of pupil diameter for a given degree of convergence is variable and the examples given are for illustration only.

Figure 3F:
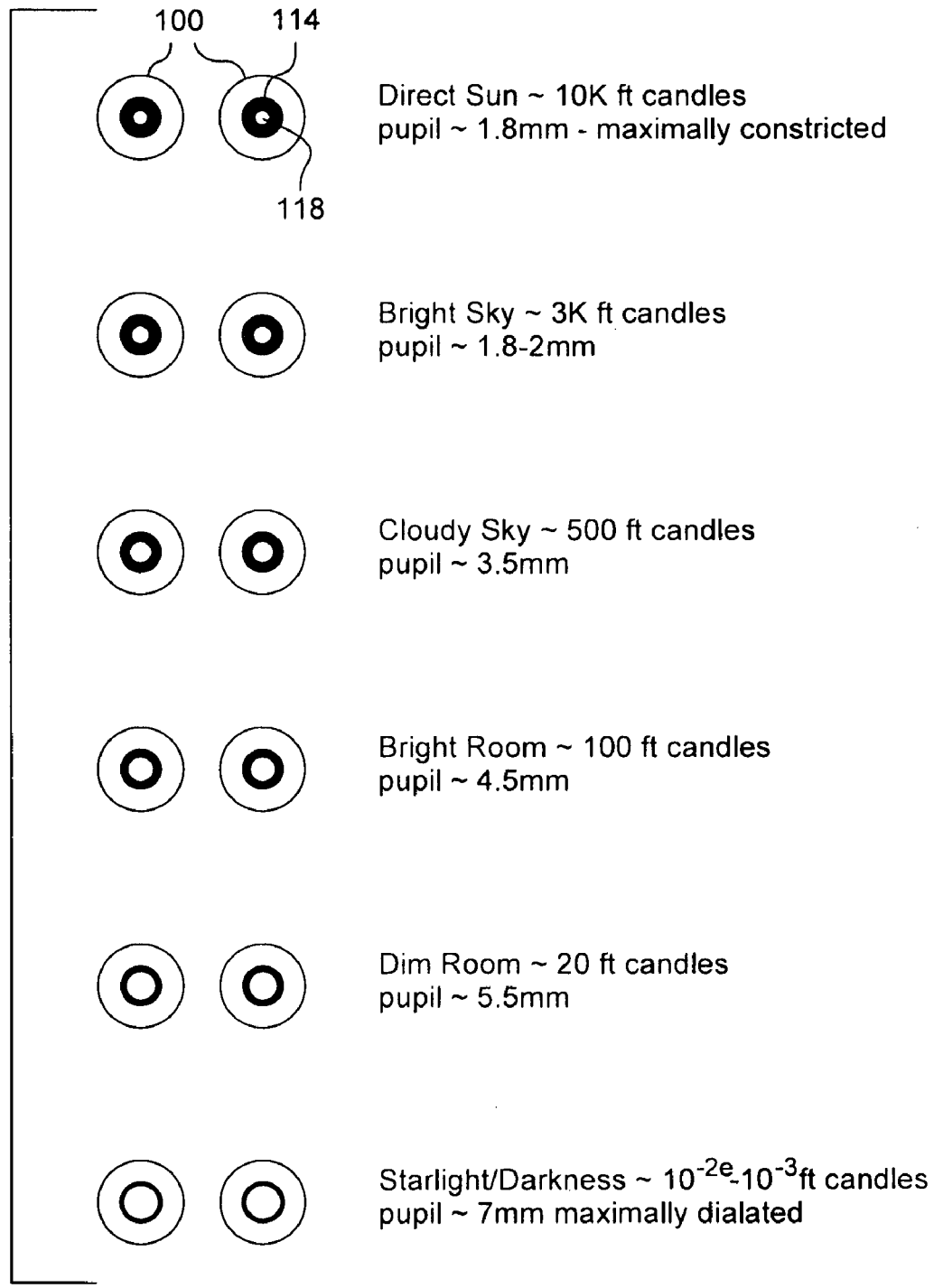

Another reflex is the pupilary brightness reflex which causes the pupil diameter to adjust to different levels of ambient brightness, generally contracting in bright light and dilating in dim light in order to maintain the optimum amount of light on the retina (i.e., retinal sensitivity). The pupil will dynamically adjust in size due to changes in ambient light conditions. Examples of the pupil diameter under various ambient light intensities are shown in FIG. 3F. This brightness response is also well understood by those skilled in the art, for instance, when the human eye 100 encounters a change in brightness, e.g., going from a dimly lit room to an outside sunny environment, the pupils 118 will contract to reduce the light intensity impinging on the retina. If the subject returns from the sunlit environment to a more dimly lit environment or room, the pupils will expand to allow for the capture of more of the ambient light.

The degree of relative brightness impinging on a surface, or the amount of illuminance is commonly expressed in units of either lumens per square foot, also known as foot-candles (ft-c), or lumens per square meter, also known as lux. Illuminance represents a photometric measurement of relative brightness conditions as perceived by the human eye. As shown in FIG. 3F, examples of different brightness conditions include direct sun (10000 ft-c or ~100,000 lux); bright sky (3000 ft-c or ~30000 lux); cloudy sky (500 ft-c or ~5000 lux), a brightly lit indoor room (100 ft-c or ~1000 lux), a room with low level of lighting (20 ft-c or ~200 lux), a very dimly lit room (0.5 ft-c or ~5 lux), and nighttime starlit darkness (0.01 ft-c or ~0.1 lux).

Although the pupil changes its diameter due to both the brightness response and the synkinetic convergence reflex, the synkinetic reflex due to convergence is the more predominant reflex (i.e., for typical everyday ranges of light levels, the synkinetic response contributes approximately nine times more than the brightness reflex to the determination of pupil diameter when viewing near objects).

As described above, because of the synkinetic reflex, the pupil size of an individual is related to the degree of convergence, and the degree of convergence is directly related to the distance from the eyes 100 to the object of regard. The closer the object is, the smaller the pupils. It is therefore possible to estimate the distance to the object of regard by determining the size of the pupil, because the size of the pupil, or change in the size of the pupil, will be indicative generally of the degree of convergence under specific levels or ranges of ambient brightness. For example, due to the synkinetic response reflex, if the distance to the object of regard is changed from 20 ft to 10 ft, the eyes must "cross" (i.e., each eye's line of sight converges) and the pupils will contract. If the object of regard is moved to 5 ft the pupils will contract to a smaller size. Likewise, if the object is brought to within 1 ft, the pupils will contract further. The relationship between the pupilary diameter and the distance to the object of regard, or degree of convergence can be measured idiosyncratically for each patient or benchmarked for an age group or other subpopulation group as discussed further below.

FIGS. 4A-C depict tabulated data showing the estimated pupil sizes at various brightness levels and convergence conditions for different population groups. The pupil diameters are measured under various brightness levels and object distance combinations to establish the data table for a respective population group. The data tables are used by the range-finder photosensor 290 to estimate the distance to the object of regard and to drive the multi-focal IOL system 210.

These measurements can be carried out using standard ophthalmologic and optometric techniques including using a pupilometer to determine pupil sizes at various distances (degrees of convergence). For example, this can be accomplished using refractometers and the like, to adjust the apparent distance to a test object thereby causing the patient to cross the eyes as they would when viewing an object at that distance, as will be apparent to those skilled in the art. The brightness response of the pupil can also be measured using standard optometric procedures, for instance, by varying the brightness impinging on the eyes of an individual, and using a pupilometer to measure the pupilary size. A baseline curve or table can be established that relates pupil size to ambient brightness.

The pupilary brightness and synkinetic responses to varying brightness conditions and object distances respectively are well understood. Generally, the degree of pupilary response, and the maximum extent to which the pupil can constrict or dilate decreases with age. Referring to the exemplary tables of FIGS. 4A and 4B, the pupils of an average 20 year old may constrict maximally to a size of 2 mm and dilate maximally to a size of 7 mm, whereas an the pupil of an average 70 year old may maximally constrict to a size of 2.5 mm and dilate maximally to a size of 5 mm. And as shown in FIG. 4C, an average 40 year old's pupils may maximally constrict to 2.3 mm and dilate maximally to 6 mm for example.

Also shown in FIGS. 4A-C are the relationships between pupil size and brightness which can be used to establish object distance for an individual patient of the population group. An intraocular sensor and processor, described below, are used to detect incident light, traversing the pupil, estimate the pupil size and relative brightness, and estimate the distance to the object of regard by comparing the measured data with the patient baseline data. This process is represented in FIGS. 7A and 7C, discussed below.

In one embodiment, an intraocular photosensor design and method is used to measure pupil diameter and changes thereto by detecting changes of incident light intensity and distribution through the pupil. The pupil 118 size can be used to derive the distance to an object of regard and this information used to adjust the focal length of the multi-focal IOL system 210.

Figure 5D:
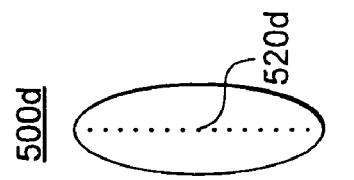
FIGS. 5A-H show example photosensor chip designs according to example embodiments of the present invention.
Figure 5C:
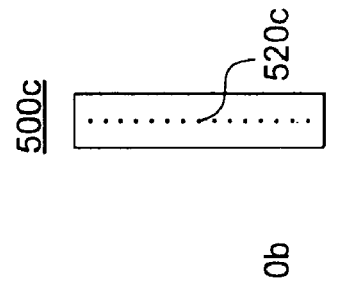
Figure 5B:
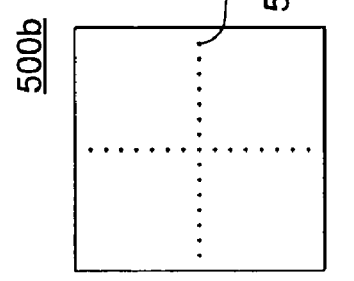
Figure 5A:
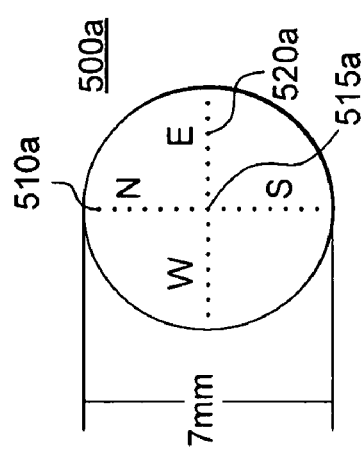
Figure 5H:
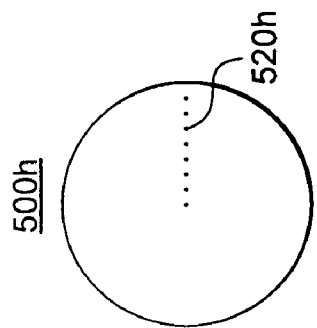
Figure 5G:
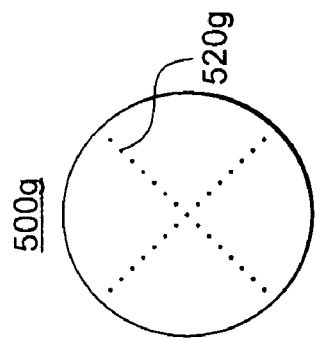
Figure 5F:
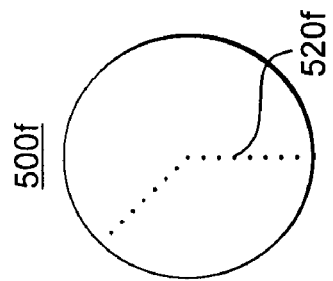
Figure 5E:
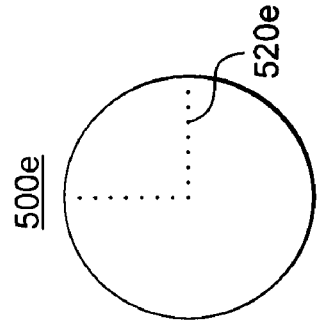

FIGS. 5A-H show various intraocular photosensor chip (or sensor array) designs 500a-500h according to example embodiments. Particularly, FIGS. 5A-H depict front views of the photosensor element designs. In one embodiment, shown in FIG. 5A, the photosensor (or photo-sensitive) elements 520a are arranged in two orthogonal linear arrays on, for instance, a semiconductor wafer or microchip. Various photosensitive materials and photosensor technologies are well known in the art and could be utilized including but not limited to charge-coupled device ("CCD") and complementary metal-oxide semiconductor ("CMOS") technologies. Referring to FIG. 5A, for illustrative purposes the "legs" 510a of the linear arrays have been labeled, N, S, E, and W, but it should be clear that any orientation of elements that can measure light intensity over an increasing linear distance (e.g., radius) from the center 515a of the photosensor chip 500a could be employed. For instance FIGS. 5B-H show other examples of photosensor element orientations on a semiconductor chip or wafer, but others are also possible as will be evident to those skilled in the art.

The photosensor chips 500a-500h in FIG. 5A-5H are approximately the size of a fully dilated pupil, e.g., 7 mm, and are oriented such that the plane of the disc of the sensor is parallel to the plane of the pupil. By matching the photosensor diameter and length of the photosensor elements 520a-520h to the maximum size of the pupil 118, the full range of pupil diameters can be monitored and detected. The photosensor chips 500a-500h could be larger or smaller depending on the desired application as will be evident to those skilled in the art.

FIGS. 6A-C show the photosensor chip 500a of FIG. 5A and its photosensor elements 520a, implanted behind the pupil 118, in various states depending on the size of the pupil 118, and how the photosensor chip 500a can be used to measure the size of the pupil 118. As shown, only those photosensor elements 520a behind the pupil receive all (or the vast majority) of photo stimulus. The photosensor's elements outside the pupil receive little or no photo stimulus.

Figure 6D:
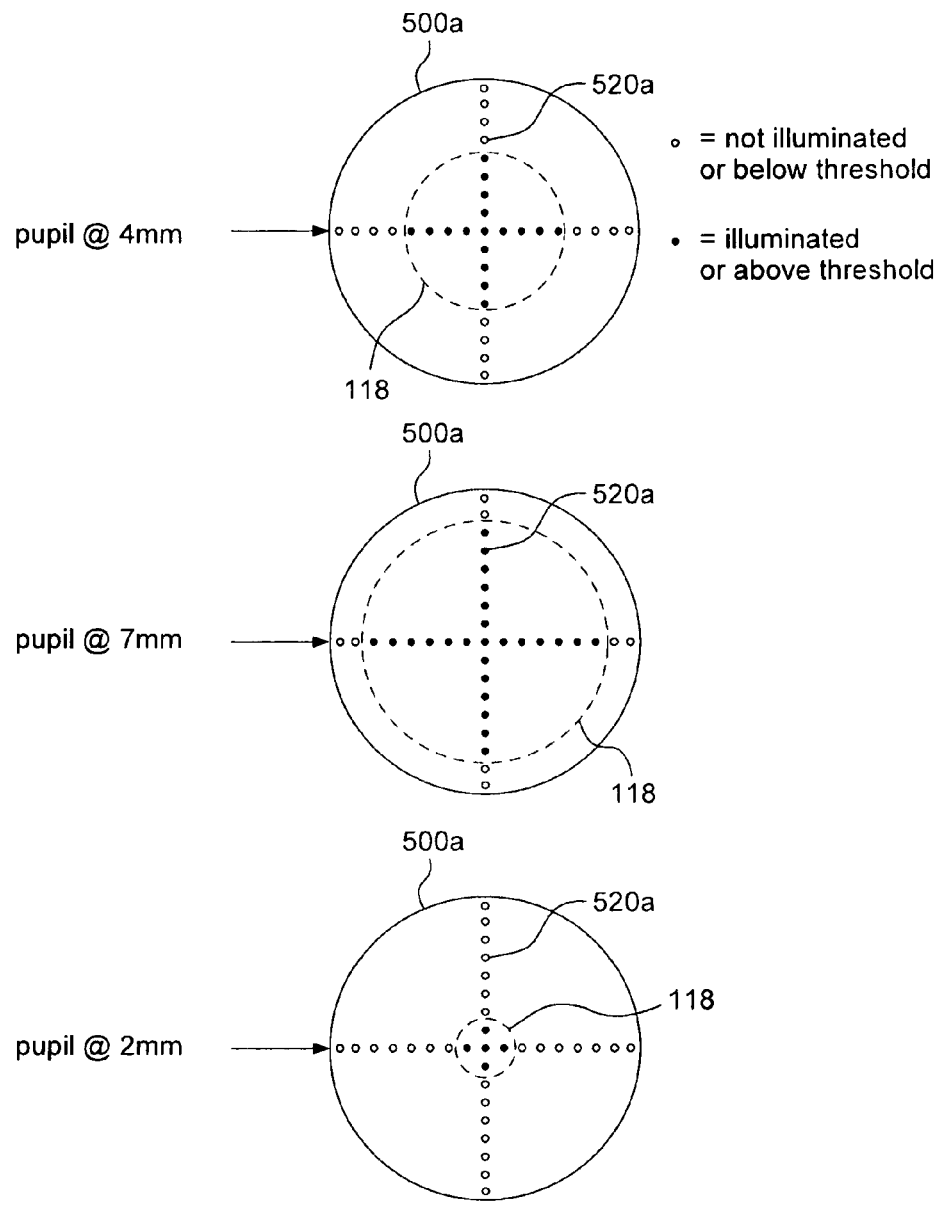
Figure 6E:
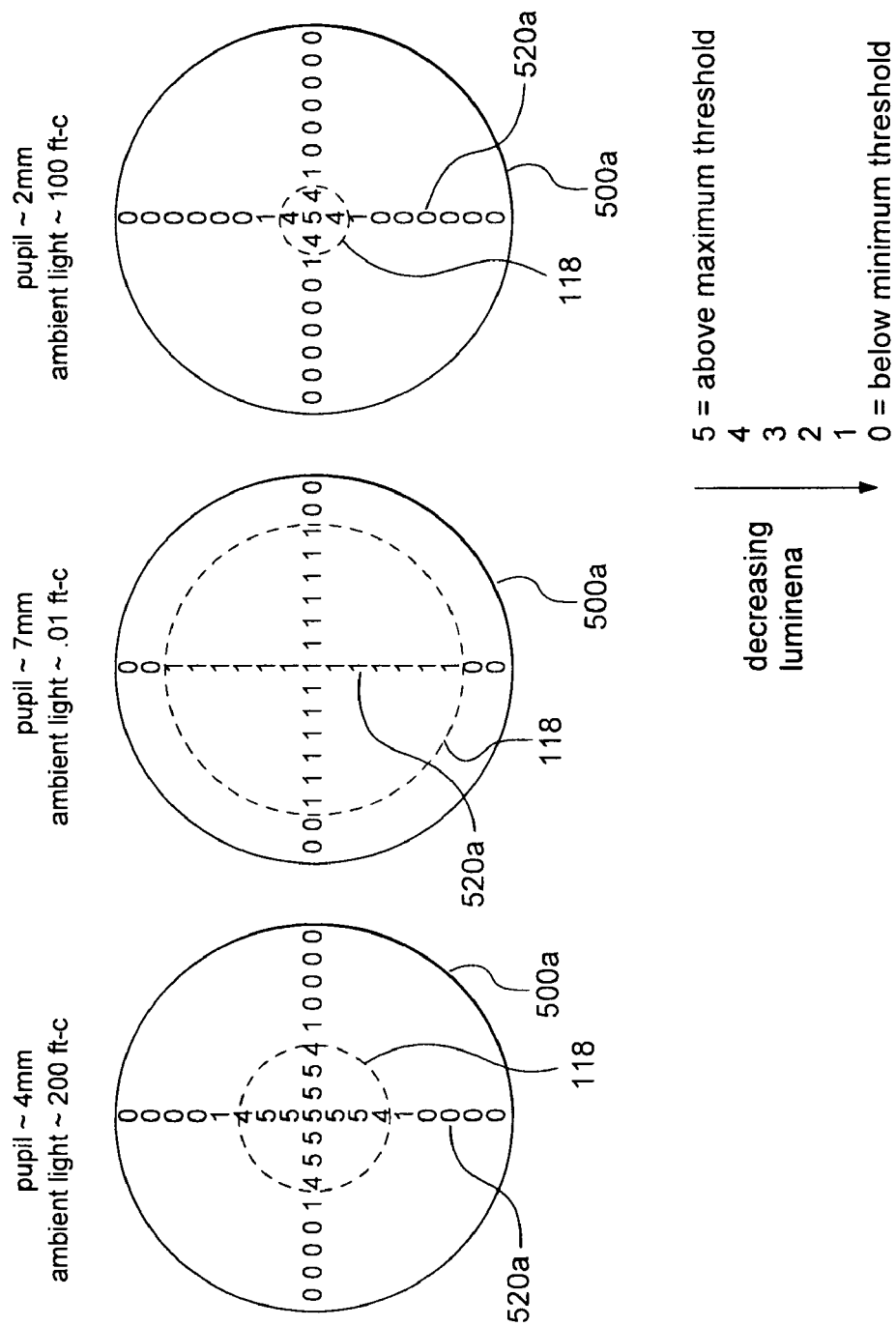
Figure 6F:
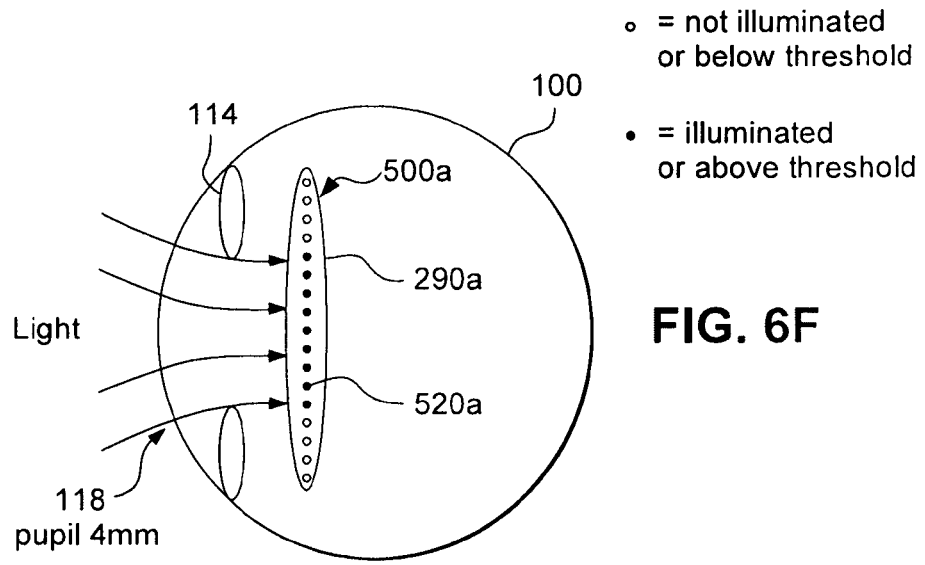
FIGS. 6F-H show a side-view of the photosensor of FIG. 5A and its elements implanted behind the pupil, in various states depending on the size of the pupil according to one embodiment of the present invention.
Figure 6G:
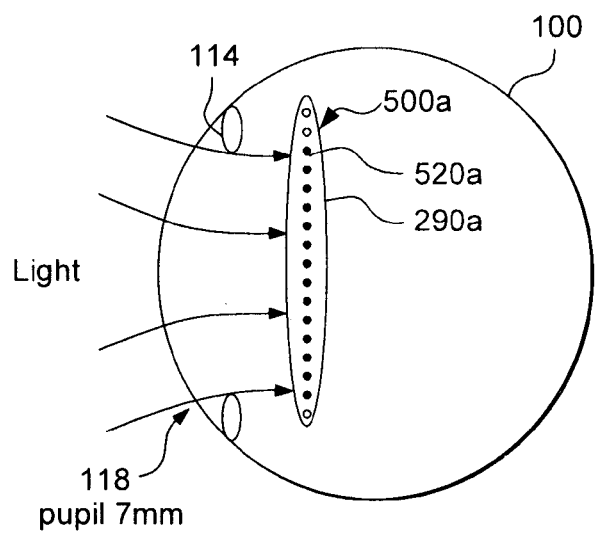
Figure 6H:
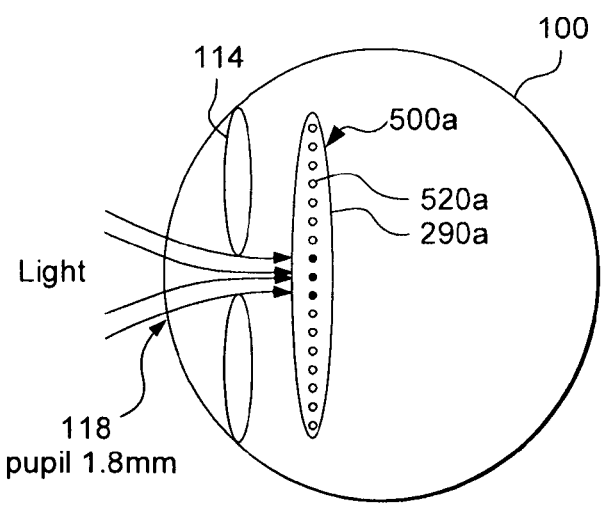

FIGS. 6F-H show a side-view of the photosensor chip 500a (FIG. 5A) and its photosensor elements 520a, implanted behind the pupil 118, in various states depending on the size of the pupil 118 corresponding to FIG. 6A-C. For clarity, the figures show only the pupil 118 and the photosensor chip 500a of the IO system (e.g., FIG. 2B, 210) behind the pupil 118, (e.g., implanted intraocularly) corresponding to the pupil diameters in FIGS. 6A-C.

FIGS. 6A and 6F show a 4 mm pupil 118 and that only the photosensor elements 520a within the central portion (4 mm circle) of the photosensor are illuminated. The photosensor elements 520a outside the pupil 118 diameter receive little or no light. FIGS. 6B and 6G show a fully dilated pupil 118 and the photosensor chip 290a in which a greater number of photosensor elements 520a are illuminated (e.g., central 7 mm circle of the sensor). FIGS. 6C and 6H show a fully contracted pupil 118 wherein only the very central portion of the photosensor chip 500a and corresponding sensor elements 520a are illuminated. Only those elements within the central approximately 2 mm area of the sensor array receive the ambient light, where those further toward the periphery receive little of no light. These values were chosen as illustrative only. Generally the diameter of pupil 118 in a healthy young adult is maintained between 2 and 7 mm, whereas the range is somewhat less in an older patient, and 4-5 mm represents and intermediate value. In each of these cases, a specific distribution of sensor elements 520a are illuminated depending on the size of the pupil 118, and the pupil size is thereby determined. Although in one embodiment, there are eight sensor elements 520a per leg 510a of the photosensor chip 500a in addition to a central photosensor element 515a, the number and orientation of the sensor elements 520a can be adjusted depending on the application.

FIGS. 6D-E show another representation of how the individual photosensor elements 520a would be "activated" depending on the pupil 118 size and light intensity. Because of different ambient light intensities, in some embodiments the sensor array can be programmed to various levels of sensitivities depending on the ambient light detected. For instance, in a dimly lit or dark environment, the photosensors elements 520a may dynamically adjust (either automatically or on instructions from a controller e.g., FIG. 2B, 270) to an increased sensitivity, whereas in a bright environment, the photosensor elements 520a may adjust to a lessened sensitivity.

FIG. 6E shows how the programmable photosensor chip 500a might register not only light distribution, but also intensity of that distribution. In one embodiment, the sensor elements 520a are programmed to register and distinguish between gradations of intensity. In this example, there are 5 different intensity levels, but as evident to those skilled in the art, the photosensor chip 500a could be designed and programmed to distinguish between any intensity in light levels. Preferably, the IOL system can distinguish between and register relative changes in light intensity to discriminate between the brightness reflex and the synkinetic reflex as discussed further herein. Also, the potential for scattered light to reach sensor elements 520a outside the area of the pupil 118 is possible, and the photosensor chip 500a can be programmed to discard such "noise" by establishing threshold levels of intensity and contrast.

The photosensor chip 500a can be designed with varying degrees of sensitivity as desired, e.g., in order to discriminate between a variety of lighting and visual conditions. Some light (e.g., scattered) may reach the photosensor elements 520a outside the pupil 118 area region. A variety of photodetectors with varying brightness and spectral sensitivities could be used as photosensors in the present embodiment. In addition, a signal processing algorithm of the received light signal can be adjusted to distinguish between different lighting conditions and distinguish between the relative amount of light received by the photosensors not within the area of the pupil and those within the area of the pupil.

As described further herein, the pupil diameter can be determined directly from the photosensor chip 500a itself (e.g., the area of the photosensor that is illumined beyond a given threshold corresponds directly to the area of the pupil 118) or determined via a post processing signal algorithm customized to the application. The pupil 118 diameters and photosensor array design 500a shown are examples only, and those skilled in the art will know that the pupil diameter can vary continuously between upper and lower limits and that the embodiment shown can readily be used to determine pupil diameter at any value between these limits, and further that other sensor designs will also operate to detect incident light and thereby determine the size of the pupil. As discussed elsewhere, in one embodiment, the pupil size measurement is used to determine the distance to an object, and this distance is used by a controller (e.g., FIG. 2B, 270) to drive the multifocal lens system 210 to adjust its focal properties to bring the view object in focus.

Because the photosensor chip (e.g., FIG. 2, 290; FIG. 5A, 500a) will be positioned posterior to the pupil 118 and anterior to the retina 136, it should be sufficiently transparent not to occlude too much of the incident light which would negatively impact vision. Thus, although the individual photosensor elements would be opaque, i.e. they would absorb the incident light, the number of sensor elements and the area they occupy is chosen such that the amount of incident light that they absorb is sufficient to distinguish between various pupil sizes, but sufficiently small relative to the overall incident light not to impact vision. In one embodiment the array is 95% transmissive. In another embodiment, the array is 90% transmissive. Other transmission profiles are possible. The photosensor chip design limits the number of photosensor elements to what is necessary to radially detect changes in incident light intensity while allowing most of the light through to reach the retina 136 (FIGS. 1, 2A) and is optimally designed to achieve the desired photosensor operation and detection while not impacting vision through photon attenuation. In one embodiment, individual sensor elements can be "turned off", e.g., electrically controlled to alter their states from a photo detector to an essentially inactive and transmissive element, thus allowing for a dynamic variation in the number of photosensor elements that are active, for instance for varying light levels, and the transmission profile of the photosensor.

Both the brightness reflex and the synkinetic reflex can affect pupil diameter. If the distance to the object of regard is constant, any change in the pupil's diameter will be primarily due to the brightness response, the response due to a change in ambient light level. Conversely, if the brightness level is relatively constant, and change in the pupil's diameter will be primarily due to the synkinetic response, the response due to a change in the distance of the object of regard. In everyday life, however, most individuals will encounter widely varying brightness level, and will also continuously shift their gaze and focus to behold objects of regard at different distances, some far off and some close up. Thus, both the brightness reflex and the synkinetic reflex may have a significant and coincident impact on causing the pupil 118 to change size according to the brightness level and the distance to the object of regard. Preferably, the IOL system 210 described above measures both brightness levels and pupil diameter, and these two data inputs, together with patient benchmark data, are used to estimate the distance to the object of regard in one embodiment.

In one embodiment, a benchmark relationship of the pupil 118 response and size to both changing brightness levels and changing distances of regard is established by measuring patient pupil diameter under a variety of brightness and convergence conditions using standard optometric techniques as already described. As described above, FIGS. 4A-C illustrate one set of measurements for different population groups, but it is to be understood that such measurements and data tabulation could be taken for individual patients and used to customize the range-finder photosensor chip 290 to each patient.

FIG. 7A illustrates an exemplary process 700a for determining the distance to an object of regard according to one embodiment, and FIG. 7C shows a look-up table for determining distance to an object of regard according to one embodiment. In block 705, an intraocular photosensor chip 290 (FIG. 2A) detects both the spatial extent and intensity of light incident through the pupil. An estimate of both pupil diameter and ambient intensity are derived in blocks 710, 715, e.g., via a processor integrated with the photosensor chip 290. The estimated pupil diameter determined in block 710 and brightness level determined in block 715 are then compared with the patient benchmark data using a comparator to estimate the distance to the object of regard, as shown in block 720. In one embodiment, the patient benchmark data (e.g., as in FIGS. 4A-C) is stored in processor memory in block 725. This data includes pupil sizes for various brightness and object distance combinations. The measured pupil size and brightness are compared in block 720 to the benchmark data stored in block 725 and an estimate of object distance is derived in block 730. An example of a look-up table for a patient is shown in FIG. 7C. For example, using the patient benchmark data of FIG. 7C, if the pupil size is estimated to be 4.1 mm and the relative brightness is estimated to be 1 ft-C, then the object distance would be estimated to be 1.2 meters. Similarly, if the pupil size is estimated to be 4.1 mm and the relative brightness is estimated to be 100 ft-C, then the object distance would be estimated to be at a distance of at least 6 meters. As will be evident to those skilled in the art, the processor comparator and distance estimator logic can be accomplished via a number of techniques including look-up tables or real-time weighted algorithmic computations.

FIG. 7B illustrates an exemplary process 700b for determining the distance to an object of regard according to another embodiment. In block 735 light entering the pupil is detected. In this embodiment, an estimate of the pupil size change and the brightness change from a prior pupil state are determined as shown in blocks 740, 745, respectively (e.g., from the measurement shown in FIG. 7A). Using patient benchmark data stored in block 725, a discriminator estimates the amount of pupil change that is due to the change in brightness, as shown in block 750. In block 755, the estimated pupil size change due to a change in object focus, near-synkinesis, is then determined and based on that estimate an estimate of the change in distance to the object of regard is determined in block 760. Discriminating between changing brightness levels and pupil size changes due to the changes allow the distance to an object of regard to be estimated as discussed further below.

A photosensor element array can exist as a separate component or be integral with other components of the IOL system. In one embodiment, shown in FIG. 8, the photosensor array is integrated with the lens element on a single chip. In this embodiment, the photosensor array 805 and electroactive lens 810 are integrated on a single semiconductive wafer 815, the chip including the photosensor elements 820, electroactive elements 825 and associated circuitry. Particularly, the electroactive lens portion of the chip 810 consists of a thin layer of electroactive lens elements 825 in the form of a pixelated array. An example of such a lens is described in U.S. Patent Publication 20060095128, incorporated herein by reference. The orientation of number of photosensor elements 820 can be adjusted depending on the application (e.g., as described above with respect to the sensor designs shown in FIGS. 5A-H).

In another embodiment, shown in FIG. 8B, the photosensor array 805 is a separate chip that is placed either on the pixelated lens array 810 (e.g., attached to the front or rear of the lens chip) or placed adjacent to the lens (in front or in back).

FIG. 9 shows other embodiments including, a photosensor 901 as part of an 10 lens system 900. This embodiment uses a non-pixelated electroactive lens 905. For example, such a lens system is described in U.S. Pat. No. 6,638,304, incorporated herein by reference. The electroactive lens 905 includes an electroactive lens material (e.g., nematic) that is attached to a transparent electrode 910. In one embodiment, the photosensor 901 is placed between the electroactive lens 905 and the transparent electrode 910. In another embodiment, the electroactive lens 905 is placed in front of the photosensor 901 lens. In another embodiment the electroactive lens 905 is placed behind the photosensor 901 (front refers to the direction oriented toward the front of the eye; i.e., closest to the pupil).

Figure 10:
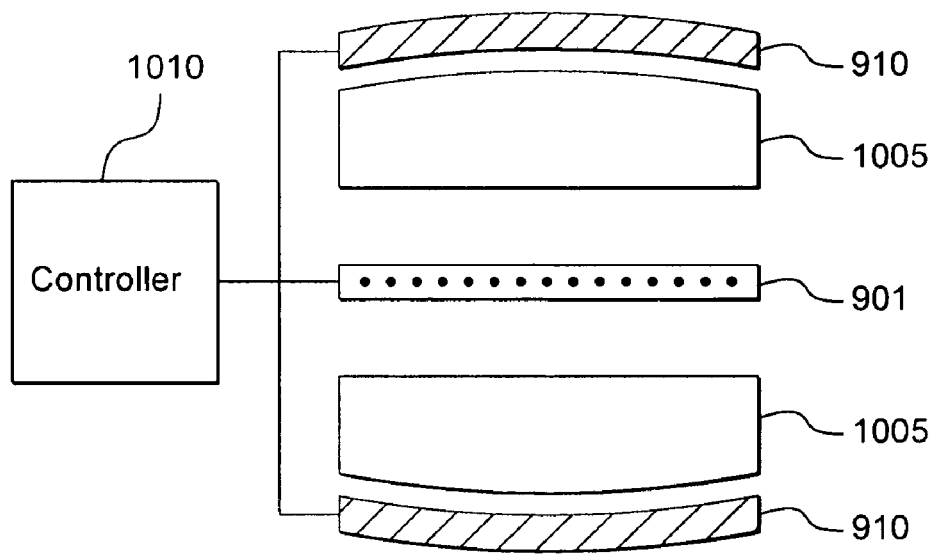
FIG. 10 shows the sensor "sandwiched" between two electroactive lens elements according to one embodiment of the present invention.

FIG. 10 shows a photosensor 901 "sandwiched" between two electroactive lens elements 1005 according to one embodiment. Also shown are two transparent electrodes 910. The electroactive lenses 1005 are controlled by a controller 1010.

Figure 11:
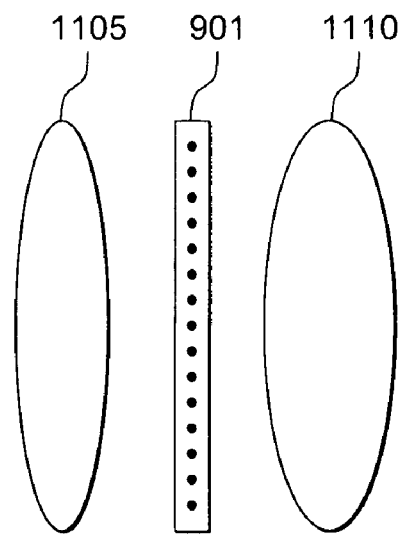
FIG. 11 shows an example non-electroactive multi-focal system using a photosensor according to one embodiment of the present invention.

In still other embodiments the photosensor array is integrated with, attached to, or placed adjacent to a variety of IOL designs, including those IOL systems which utilize non-electroactive lenses, including deformable lenses that are deformably adjusted via mechanical or other forces, movable lens systems including multi-lens system, and generally with any lens system capable of adjusting its focal length. FIG. 11 shows an example of how a photosensor 901 would be used with a non-electroactive multi-focal system including a fixed lens 1110 and a focusing lens 1105.

Figure 12:
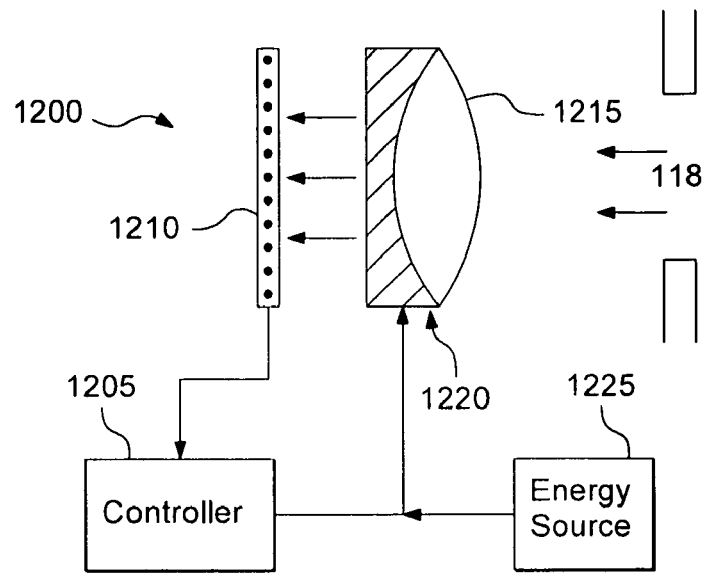
FIG. 12 shows an IOL system according to one embodiment of the present invention.

In one embodiments shown in FIG. 12, a photodetector sensor array is integrated with a multi-focal lens optic and associated controller and actuator, and used to determine the range to an object of regard, the relative ambient brightness level and changes thereto, or both. The sensor array is a programmable array in one embodiment. The degree and distribution of illumination of the sensor elements is indicative of the light distribution and intensity at any given moment traversing the pupil, and this data is used to determine the size of the pupil at or near that moment. In one embodiment, the number of or pattern of photosensor elements that are activated (i.e., receiving above threshold light intensity) and in some cases the degree of light intensity is used directly by the controller to drive the lens element. In another embodiment the data representing the illumined photosensor elements is further processed, for example by algorithmic processing or compared with a look-up table, to determine the distance to the object of regard, e.g., by determining the pupil size and deriving the object distance from a known pupil response baseline.

Particularly, FIG. 12 shows a block diagram of an IOL system 1200 including sensor 1210 for detecting incident light and for determining pupil size, or a change in ambient light intensity, or both, to derive the distance to the object of regard. A microcontroller 1205 for data processing and instruction control, an actuator 1220 for driving the focusing element, and the multi-focal lens element 1215 are also included. A power source (or energy source) 1225 supplies power to the controller 1205, the range finding photosensor 1210, and the actuator 1220.

Figure 13:
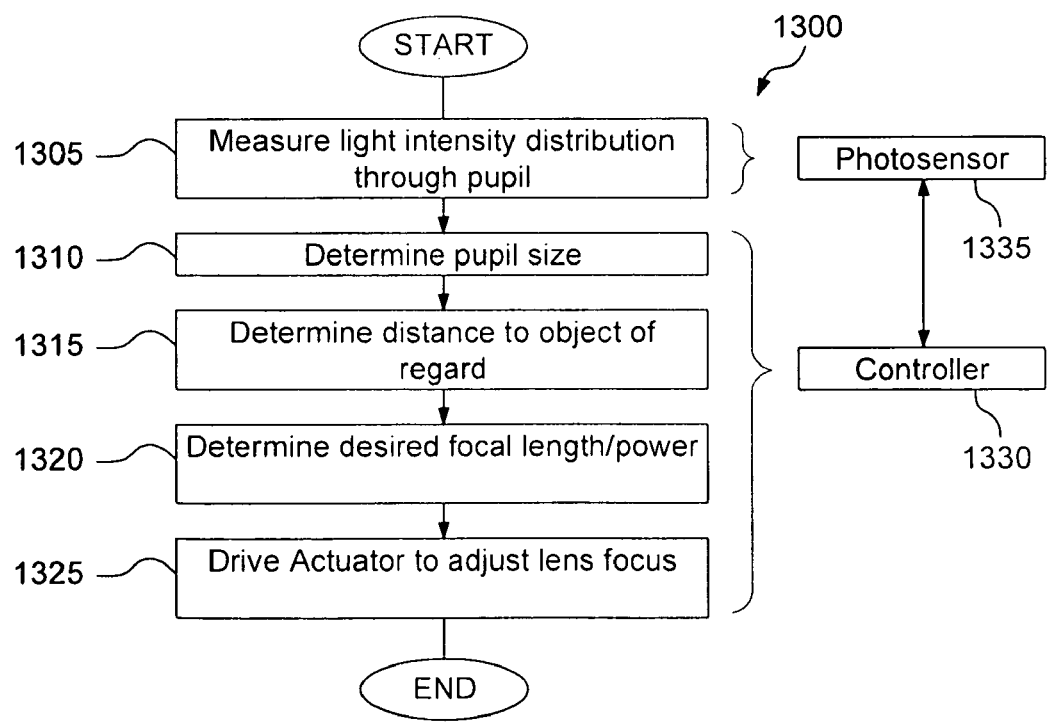
FIG. 13 shows an example general process for determining a distance to an object of regard and adjusting the multi-focal lens system using an IO photosensor to measure pupil size and determine distance to object of regard according to one embodiment of the present invention.

FIG. 13 shows the process 1300 for determining a distance to an object of regard and adjusting the multi-focal lens system according to one embodiment. At block 1305, the light distribution received through the pupil is measured. Pupil size based on the incident light is determined at block 1310. In turn, distance to an object of regard based on pupil size is determined at block 1315 and at block 1320 the focal length of the lens system appropriate for the object distance is determined. At block 1325 an actuator is driven to adjust lens focus.

As shown in FIG. 13, the microcontroller 1330 is encoded with instructions for performing blocks 1310-1325 of process 1300. This can be implemented in firmware or software. In an embodiment the instructions are encoded directly in hardware (e.g., an asic). The instructions can be encoded on a single chip along with the pixelated array (not shown) and photosensor 1335. The instructions on the microcontroller include instructions for receiving data from the photosensor 1335 data and for determining the distance to the object of regard. For example, the raw data from the photosensor 1335 may cause the microcontroller 1330 to issue instructions to the actuator, which then actuates the lens system to effect the focal length change. In such an arrangement, a specific group or orientation of activated or illumined elements of the photosensor 1335 cause the focusing instruction of the microcontroller 1330 to be executed. This functionality can be implemented via a look-up table or similar. The table would represent a mapping between sensor element illumination patterns (representing a target distance) and the focal power needed from the lens system.

Alternatively, the data from the photosensor 1335 may be processed further by the microcontroller 1330 and the results of this post-processing computation used by the microcontroller 1330 to instruct the actuator, which alters the focal length of the system. The overall operation and result is that based on the input from the photosensor, the distance to the object of regard is determined or estimated and the necessary focusing power determined and the actuator driven to act on the lens system in order to change its index of refraction in order to obtain the desired power. A power source supplies power to the controller, the range finding photosensor, and the actuator. A single power source can supply all three, e.g., in the case of an integrated range finder sensor, actuator and lens system, or separate power sources can provide each component with power. The power supply for the system can be a rechargeable energy storage device such as a battery, capacitor, or other energy store as are well known in the art. Examples of energy generation means include photoelectric, thermoelectric, and piezoelectric transducers capable of capturing photonic, thermal, and mechanical energy respectively, for use or storage by the system. Energy transfer and storage by inductively coupling, laser or RF energy are other examples, but the invention is not limited to any specific power generation or storage means.

The IOL system in one embodiment has continuously varying focal properties and powers. In another embodiment the lens system is limited to a number of specific focal powers. For example, the system may be configured to adjust continuously in 0.1 D increments between +2 and −10 D, or the system may be designed to have only 3 different focal powers, e.g., 0 D for distance vision, 1 D for intermediate vision and 3 D for near vision. Depending on the specific application or desire, a wide range of options are available from the system, including the degree of exactness in determining the distance to the object of regard, and the range and sensitivities and ability to tune the focusing power of the system.

As described above, accurate determination of the distance to objects of regard can be accomplished by measuring the pupil size and ambient brightness level and comparing those measurements against an empirically established patient pupil size baseline. This range-finding capability coupled with a adjustable multi-focal lens system allows the lens system to be appropriately adjusted to focus on the object of regard. Patient or population baselines relating pupil size and changes in pupil size in response to changing brightness and changing object distances can also be created to allow for further refinement and accuracy in range-finding. As described below, the change in the intensity of illumination of individual photosensors provides a measure of the changes in ambient brightness, and this data can be used discriminate between the pupilary reflex responses, and resolve ambiguities.

For instance, an individual may be transitioning from one level of brightness to another level of brightness, the change in brightness level causing a significant pupilary brightness response. For instance, leaving an indoor environment and walking outside into bright sunlight, or turning on a bright light in a previously darkened room, could result in several orders of magnitude change in ambient brightness and significant pupilary constriction. The converse of these situations, i.e., proceeding from a brightly lit environment, to relative darkness would potentially result in significant pupilary dilation. In these circumstances, the pupilary brightness response may temporarily (e.g., until the retina adjusts) dominate the synkinetic response and the rapid change in pupil diameter would not necessarily be an indication that the distance to the object of regard has changed, but rather that the level of brightness has changed.

In one embodiment, temporal changes in brightness levels of individual sensor elements are measured and used to distinguish and resolve any potential ambiguities. By measuring the change in relative brightness as a function of time at each individual sensor element allows the system to determine, for instance, whether brightness is increasing or decreasing.

FIGS. 14A-F show hypothetical scenarios that may result in the pupil changing size due to the brightness reflex, and how the range-finder photosensor would distinguish pupilary response due to brightness level changes. The number of photosensor elements 520 that are illuminated above a threshold level provides information to determine pupil size. The change in the intensity of illumination at each sensor element indicates changes in ambient light level.

FIG. 14A shows a pupil diameter of 4 mm of a subject's eye while viewing an object at 1 m (1 diopter) in a bright room, e.g., a brightness of 100 ft-c. The central photosensor elements 520, corresponding to pupil diameter of 4 mm, are illuminated with a relative intensity of 100. This pupil diameter of 4 mm in a relative brightness of 100 corresponding to a object of regard distance of 1 m—requiring 1 diopter of convergence accommodation may be obtained from the individual patient baseline measurements as discussed above according to one embodiment. FIG. 14B shows a case where the room light is dimmed to 10 ft-c, which, for example, causes the pupil to dilate to 5 mm. Additional peripheral photosensor elements are illuminated due to the increase pupil size, however, the relative intensity of the central sensors, corresponding to the original pupil size of 4 mm, drops to 10. This decrease in intensity of the inner sensor elements and concurrent increase in the number of photosensor elements 520 illuminated indicates to the system that the pupil dilated because of a decrease in relative brightness, and not because the distance to the object of regard had changed. A similar effect is shown in FIG. 14C where the light is further dimmed to 1 ft-c. In this case, the pupil dilates and the number and radial extent of photosensor elements 520 illuminated increase, thereby indicating an enlargement of the pupil while the sharp decrease in luminance to a relative value of one (1) indicates that pupil dilatation was due to the change in brightness level and not a change in the distance to the object of regard. The range-finding system or controller in this situation, according to one embodiment, would correlate the pupil change with the change in relative brightness, and not due to a change in distance to the object of regard, and the IO multi-focal system would not alter the focal length in is instance.

FIG. 14D shows a pupil diameter of 4 mm of a subject's eye while viewing an object at 1 m (1 diopter) in a bright room, e.g., a brightness of 100 ft-c. The central photosensor elements 520, corresponding to a pupil diameter of 4 mm, are illuminated with a relative intensity of 100. FIG. 14E shows the case where the room light is brightened to 500 ft-c, which, for example, causes the pupil to contract to 5 mm. The most peripheral photosensor elements 520 that were illuminated at 100 f ft-c are no longer illuminated due to the decrease in pupil size caused by the brightness reflex. However, the relative intensity of the central photosensor elements, corresponding to the new pupil size of 3 mm, increase to 500. This increase in intensity of the inner photosensor elements and concurrent decrease in the number of sensors illuminated indicates to the system that the pupil contracted because of an increase in relative brightness, and not because the distance to the object of regard had changed. A similar effect is shown in FIG. 14F where the pupils encounter a light intensity increased to 2500 ft-c (e.g., bright sky). The pupil constricts, perhaps maximally, and the number and radial extent of photosensor elements 520 illuminated decreases, thereby indicating the contraction of the pupil, while the sharp increase in relative luminance to a value of 2500 indicates that pupil contraction was due to the change in brightness level, and not a change in the distance to the object of regard. The range-finding system or controller in this situation, according to one embodiment, would correlate the pupil change with the change in relative brightness, and not due to a change in distance to the object of regard, and the IO multi-focal system would not alter the focal length in is instance.

Generally, these embodiments provide a way to accurately determine the range to an object of regard utilizing an intraocular photosensor and processor to measure pupil size and determine object distance while taking into account changes in ambient brightness levels. If the relative brightness increases or decreases significantly and rapidly enough such that the pupilary brightness reflex contributes a significant amount to pupilary size change, the system will estimate or determine whether and to what extent the pupilary contraction or dilation is due to brightness reflex versus the synkinetic reflex, and thereby accurately and continuously determine the distance to the object of regard even under conditions of changing relative brightness.

Figure 15:
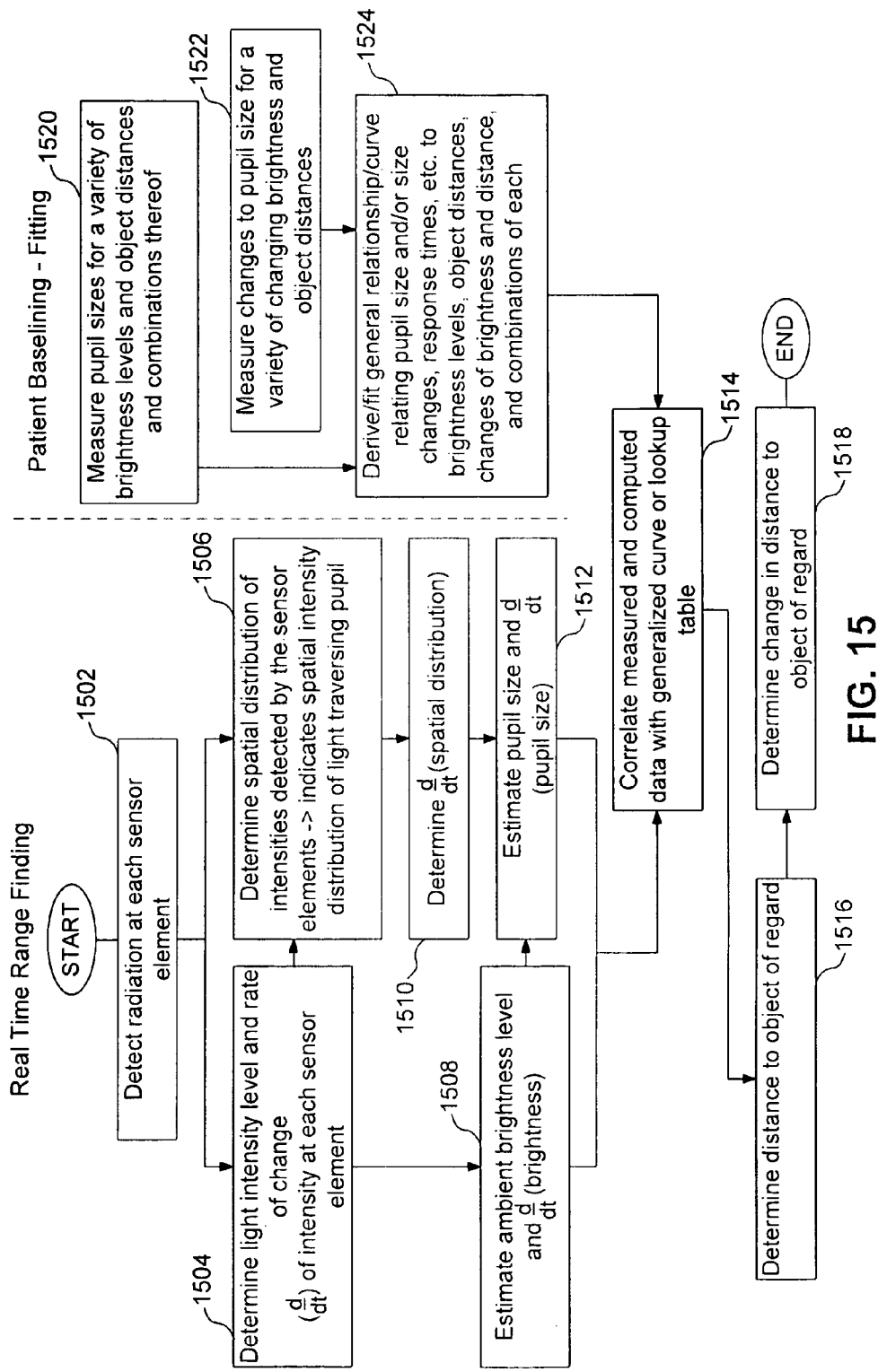
FIGS. 15 and 16 show an example process flow diagram for discriminating between brightness and synkinetic reflex in order to determine the distance to an object of regard.
Figure 16:
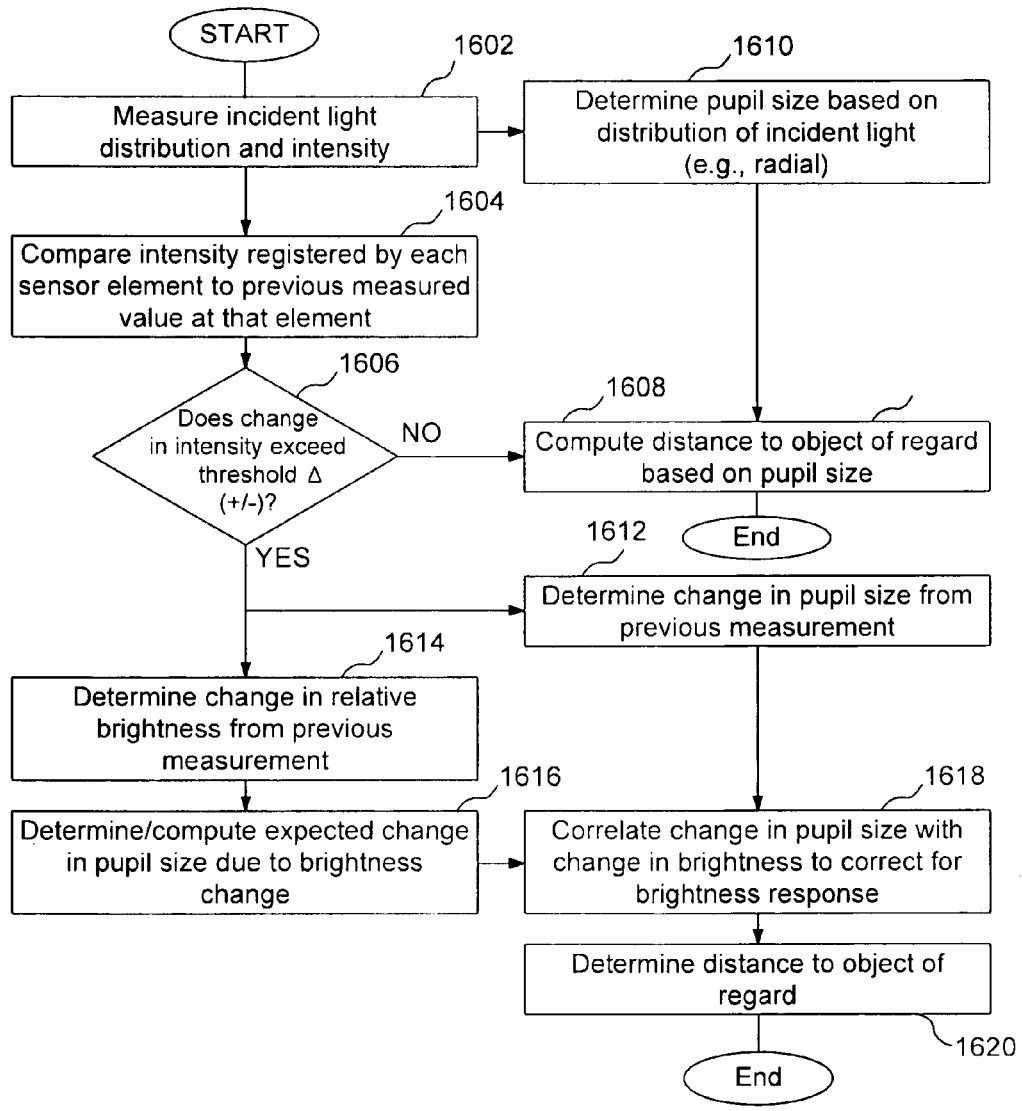

FIGS. 15 and 16 shows example generalized process flow diagrams according to other embodiments for determining distance to objects of regard under varying conditions of brightness. Each involve initially establishing an individual patient or population group baseline, of pupil size and changes thereto in relation to varying and changing brightness and near-converge scenarios. These baselines can be created for example through empirical measurements in the clinician's office or with reference to the literature, and the baseline can include as many or as few parameters and data points as necessary for the specific application need and sensitivity. The baselines are used as programming input to the IO range-finder system, which comprises a sensor unit for measuring light which has traversed the pupil and estimating, the size of the pupil, the relative brightness level, and changes to those physical variables. As will be evident to those skilled in the art a variety of mathematical methods, including weighted algorithms, neural networks, and others known in the art could be used to establish such baselines and a variety of processing means (e.g., asic) could be used to implement the correlation functionality correlating the baseline to the measured intraocular light distribution and intensity changes.

Referring to FIG. 15, at block 1502, radiation at each sensor element is detected. At block 1504 a light intensity level and a rate of change d/(dt) of intensity at each sensor element is determined, which is fed to block 1506. As shown in FIG. 15, blocks 1504 and 1506 can be two separate processes operating in parallel. Block 1506 determines a spatial distribution of intensities detected by the sensor elements and indicates a spatial intensity distribution of light traversing the pupil. A change in the spatial distribution, d/(dt) (spatial distribution) is determined at block 1510. Block 1512 uses the information obtained in block 1510, along with an estimation of ambient brightness level and a change in brightness, d/dt (brightness), obtained in block 1508, to estimate pupil size and a change in pupil size, d/(dt) (pupil size).

At block 1520 a patient baseline is initiated by measuring pupil sizes for a variety of brightness levels and object distances and combinations thereof. At block 1522 (either in parallel or sequentially), changes to pupil size for a variety of changing brightness and object distances are measured. Based on the information obtained from blocks 1520 and 1522, at block 1524, a general relationship or curve relating to pupil size and/or size changes, response times, etc., are derived and/or fitted, as the case may be, to brightness levels, object distances, changes of brightness and distance, and combinations of each. At block 1514 the measured and computed data are correlated with a generalized curve or lookup table and at block 1516 the distance to the object of regard is determined. At block 1518 a change in the distance to the object of regard is determined.

Referring to FIG. 16, at block 1602 incident light distribution and intensity are measured and at block 1604 the intensity registered by each sensor element to a previous measured value at that element is compared. In addition, at block 1610 a pupil size is determined based on the distribution of incident light (e.g., radial). A determination is made at block 1606 whether a change in intensity exceeds a threshold Δ (+1/−). If not, then at block 1608 a distance to an object of regard is computed based on pupil size.

If the change exceeds the threshold, then at block 1612 a change in relative brightness is determined from previous measurement and at block 1618 an expected change in pupil size due to brightness change is determined (or computed). Following from blocks 1612 and 1616, at block 1620, a change in pupil size is correlated with a change in brightness to correct for brightness response. Based on this information at block 1622 a distance to object of regard is determined.

In one embodiment the pupil size of each patient is measured under 9 different conditions of light intensity and distance (convergence) in order to establish the patient pupil response baseline; the pupil size is measured at low, medium, and high levels of brightness (e.g., 0.01, 25, 100 ft-c) for each of the 3 distance measurement (20 ft, 10 ft, 1 ft). In another embodiment, only 2 measurements of brightness are taken for each distance. In yet another embodiment, 6 levels of brightness are measured, for each of 6 different distances, requiring a total of 36 measurements. Any number of combinations is possible depending on the application and sensitivity. The data obtained can be interpolated and extrapolated to obtain a relationship curve covering each combination of brightness and distance to object as will be evident to those skilled in the art. In some embodiments, experimental data is obtained and corresponding pupil response relationships are established for the general population, population subgroups, and individual patients. Experimental data could be obtained and corresponding relationships between pupil size and brightness level could be established for the general population, population subgroups, for example based on age, or individual patients, and these data used to provide various levels of customization and fine-tuning of focusing depending on the individual or population group.

In another embodiment, not only is the resulting pupil size determined for a variety of lighting and target distance combinations, but the actual pupil response, e.g., how it changes in size, the speed and degree of overshoot or fine-adjustment with concurrent or near-concurrent changes in both light level and target distance are measured and these data used to more accurately determine an individual's baseline response for most real-world conditions.

By benchmarking and establishing individual or population specific pupilary response that take into account both the effect of the relative brightness and object distance on pupil diameter allows for accurate determination of the distance to the object of regard in a variety of lighting conditions utilizing embodiment of the invention. In one embodiment, each IOL system is customized to each individual patient, by programming the IO controller such that the pupil sizes determined in various light levels will result in accurate determination of object distances and result in optimum focus for that individual patient.

Although this invention has been illustrated by reference to specific embodiments, it will be apparent to those skilled in the art that various changes and modifications may be made which clearly fall within the scope of the invention. The invention is intended to be protected broadly within the spirit and scope of the appended claims.

What is claimed is:

1. A method for determining the distance to an object of regard, comprising the steps of:
    measuring a size of a pupil of an eye regarding an object; and
    estimating the distance to the object of regard based on the measured pupil size,
    wherein measuring the size of the pupil is accomplished by measuring at least one of an amount and a distribution of light traversing the pupil.

2. The method of claim 1, wherein measuring the at least one of the amount and the distribution of light traversing the pupil is accomplished by a photosensor implanted in the eye, and estimating the pupil size and distance to an object of regard is performed by a processor.

3. The method of claim 1, further comprising the step of:
    estimating a change in ambient brightness impinging on the eye by detecting changes in an intensity of light traversing the pupil.

4. The method of claim 1, further comprising the step of:
    estimating the amount of pupil size change due to a change in ambient brightness.

5. A method for determining the distance to an object of regard, comprising the steps of:
    measuring a size of a pupil of an eye regarding an object;
    estimating the distance to the object of regard based on the measured pupil size; and
    estimating the degree of ocular convergence using the size of the pupil to estimate the distance to the object of regard.

6. The method of claim 5, further comprising the step of:
    discriminating between a pupil size change due to an ambient brightness change and a change in distance to an object of regard, wherein the accuracy of the distance to the object of regard based on pupil size is not substantially affected due to a change in ambient brightness.

7. A method for determining the distance to an object of regard, comprising the steps of:
    measuring a size of a pupil of an eye regarding an object;
    estimating the distance to the object of regard based on the measured pupil size;
    establishing a plurality of individual baseline relationships between at least one of (a) respective pupil sizes and object of regard distances and (b) respective ambient brightness levels among individual patients or patient populations; and
    estimating the distance based on the pre-established relationship,
    wherein estimating of changes in pupil sizes, ambient brightness, and distances are accomplished using a programmable photosensor and processor.

8. The method of claim 7, wherein the programmable photosensor is implanted intraocularly.

9. A method of estimating the distance to an object of regard for use in adjusting a focal length in an intraocular multi-focal lens system, comprising:
    detecting a photonic energy entering a pupil of an eye;
    estimating a pupil size based on the distribution of the photonic energy obtained during the detecting; and
    estimating the distance to the object of regard based on the pupil size.

10. The method of claim 9, wherein the pupil represents an estimate of a degree of ocular convergence.

11. The method of claim 9, further comprising:
    estimating changes in light intensity impinging on the eye and corresponding changes in the pupil size; and
    estimating the distance to the object of regard based on pupil size changes due to changes in brightness.

12. A method for detecting changes in relative brightness impinging on a human visual system, comprising:
    measuring a first distribution of photonic energy that has entered an eye through a pupil;
    detecting a change in intensity of at least one portion of the first distribution; and
    estimating a relative change in brightness impinging on the eye.

13. The method of claim 12, wherein the measuring of the first distribution of photonic energy is accomplished using an intraocular photosensor comprising a plurality of sensor elements.

14. The method of claim 12, further comprising:
    implanting a programmable photosensor in the eye; and
    estimating the pupil size and distance to an object of regard using a processor.

15. The method of claim 12, wherein estimation of changes in pupil sizes, ambient brightness, and estimation of distances are accomplished using a programmable photosensor and a processor, both the programmable photosensor and the processor being implanted within the eye wherein a relative light intensity of a first set of sensor elements illuminated at a first time is less than a light intensity of the first set of sensor elements illuminated at a second time thereby indicating a decrease in ambient brightness.

16. A method for estimating a distance to an object of regard under conditions of changing ambient brightness, comprising:
   measuring a first spatial distribution and an intensity of photonic energy that has entered an eye through a pupil at a first time;
   measuring a second spatial distribution and an intensity of photonic energy that has entered an eye through the pupil at a second time;
   estimating a pupil size at the first time and the pupil size at the second time;
   estimating a change in pupil size between the first time and the second time;
   estimating a change in the intensity of light incident on the pupil at the first time and at the second time; and
   estimating at least one of the distance to an object of regard and a change in distance to the object of regard.

17. The method of claim 16, wherein the distance to the object of regard is estimated, at least in part, by utilizing a relationship between the pupil size and a change in the pupil size, and a degree of ocular convergence and a change in the degree of ocular convergence.

18. The method of claim 16, further comprising:
   estimating an amount of pupil size change due primarily to a change in light intensity impinging on the eye at the first time and at the second time, and taking into account the change in pupil size between the first time and the second time due primarily to a change in brightness to estimate the degree of at least one of an ocular convergence and a near-synkinesis to estimate the distance to the object of regard.

* * * * *